US009381042B2

(12) United States Patent
Ross et al.

(10) Patent No.: US 9,381,042 B2
(45) Date of Patent: Jul. 5, 2016

(54) EXTERNAL FIXATION CONNECTION ROD FOR RAPID AND GRADUAL ADJUSTMENT

(71) Applicant: Texas Scottish Rite Hospital for Children, Dallas, TX (US)

(72) Inventors: John David Ross, Ovilla, TX (US); Mikhail L. Samchukov, Coppell, TX (US); Alexander M. Cherkashin, Flower Mound, TX (US); John G. Birch, Dallas, TX (US)

(73) Assignee: TEXAS SCOTTISH RITE HOSPITAL FOR CHILDREN, Dallas, TX (US)

( * ) Notice: Subject to any disclaimer, the term of this patent is extended or adjusted under 35 U.S.C. 154(b) by 117 days.

(21) Appl. No.: 14/071,333

(22) Filed: Nov. 4, 2013

(65) Prior Publication Data

US 2014/0135764 A1    May 15, 2014

Related U.S. Application Data

(63) Continuation of application No. 13/675,961, filed on Nov. 13, 2012, now Pat. No. 8,574,232.

(51) Int. Cl.
*A61B 17/00* (2006.01)
*A61F 4/00* (2006.01)
(Continued)

(52) U.S. Cl.
CPC .................. *A61B 17/66* (2013.01); *A61B 17/62* (2013.01); *A61F 5/042* (2013.01)

(58) Field of Classification Search
CPC ........ A61B 17/60; A61B 17/62; A61B 17/64; A61B 17/66
USPC .............. 606/53–59, 246, 250–253, 260, 278
See application file for complete search history.

(56) References Cited

U.S. PATENT DOCUMENTS 2,238,870 A    4/1941    Haynes
2,346,346 A    4/1944    Anderson
(Continued)

FOREIGN PATENT DOCUMENTS

CA    2633944 A1    7/2007
DE    3802743 A1    8/1989
(Continued)

OTHER PUBLICATIONS

Extended European Search Report, EP 09708841.3-1654 / 2240085; PCT/US2009/033603, dated Dec. 2, 2013, 5 pages.
(Continued)

*Primary Examiner* — Ellen C Hammond
*Assistant Examiner* — Christina Negrellirodrigue
(74) *Attorney, Agent, or Firm* — Baker & McKenzie LLP

(57) ABSTRACT

An external fixation connection rod that allows for rapid and gradual length adjustment. In some embodiments, the fixation connection rod includes an inner sleeve received within a telescopic rod to allow for rapid adjustment of an overall length of the fixation connection rod. In some embodiments, the fixation connection rod includes an adjustment mechanism to allow for gradual adjustment of the overall length of the fixation connection rod by lengthening or shortening a threaded elongated member within the inner sleeve, and the adjustment mechanism includes a first rotation member, a second rotation member, and a spring. Distal translation of the first rotation member relative to the second rotation member allows the adjustment mechanism to move from a first, locked position to a second, unlocked position, allowing the first rotation member and the second rotation member to rotate about the inner sleeve and the threaded elongated member during gradual adjustment.

18 Claims, 9 Drawing Sheets

(51) Int. Cl.
  *A61F 5/04* (2006.01)
  *A61B 17/66* (2006.01)
  *A61F 5/042* (2006.01)
  *A61B 17/62* (2006.01)

(56) References Cited

U.S. PATENT DOCUMENTS

| | | | |
|---|---|---|---|
| 4,308,863 A * | 1/1982 | Fischer | 606/57 |
| 4,365,624 A | 12/1982 | Jaquet | |
| 4,621,627 A | 11/1986 | DeBastiani et al. | |
| 4,768,524 A | 9/1988 | Hardy | |
| 4,889,111 A | 12/1989 | Ben-Dov | |
| 4,973,331 A | 11/1990 | Pursley et al. | |
| 4,988,244 A | 1/1991 | Sheldon et al. | |
| 5,019,077 A | 5/1991 | De Bastiani et al. | |
| 5,095,919 A | 3/1992 | Monticelli et al. | |
| 5,156,605 A | 10/1992 | Pursley et al. | |
| 5,180,380 A | 1/1993 | Pursley et al. | |
| 5,458,599 A | 10/1995 | Adobbati | |
| 5,533,418 A | 7/1996 | Wu et al. | |
| 5,702,389 A | 12/1997 | Taylor et al. | |
| 5,728,095 A | 3/1998 | Taylor et al. | |
| 5,776,132 A | 7/1998 | Blyakher | |
| 5,863,292 A | 1/1999 | Tosic | |
| 5,885,283 A | 3/1999 | Gittleman | |
| 5,891,143 A | 4/1999 | Taylor et al. | |
| 5,928,230 A | 7/1999 | Tosic | |
| 5,971,984 A | 10/1999 | Taylor et al. | |
| 6,030,386 A | 2/2000 | Taylor et al. | |
| 7,282,052 B2 * | 10/2007 | Mullaney | A61B 17/6458 606/59 |
| RE40,914 E | 9/2009 | Taylor et al. | |
| 8,029,505 B2 | 10/2011 | Hearn et al. | |
| 8,202,273 B2 | 6/2012 | Karidis | |
| 8,257,353 B2 | 9/2012 | Wong | |
| 8,296,094 B2 | 10/2012 | Harrison et al. | |
| 8,333,766 B2 | 12/2012 | Edelhauser et al. | |
| 8,366,710 B2 | 2/2013 | Hirata et al. | |
| 8,377,060 B2 | 2/2013 | Vasta et al. | |
| 8,388,619 B2 | 3/2013 | Mullaney | |
| 2002/0010465 A1 | 1/2002 | Koo et al. | |
| 2003/0149378 A1 | 8/2003 | Peabody et al. | |
| 2003/0191466 A1 | 10/2003 | Austin et al. | |
| 2003/0199856 A1 | 10/2003 | Hill et al. | |
| 2003/0212398 A1 | 11/2003 | Jackson | |
| 2004/0073211 A1 | 4/2004 | Austin et al. | |
| 2004/0097922 A1 | 5/2004 | Mullaney | |
| 2004/0116926 A1 | 6/2004 | Venturini et al. | |
| 2005/0192572 A1 | 9/2005 | Abdelgany et al. | |
| 2005/0215997 A1 | 9/2005 | Austin et al. | |
| 2005/0234457 A1 | 10/2005 | James et al. | |
| 2006/0052782 A1 | 3/2006 | Morgan et al. | |
| 2006/0207118 A1 | 9/2006 | Kim | |
| 2006/0235389 A1 | 10/2006 | Albert et al. | |
| 2007/0055234 A1 | 3/2007 | McGrath et al. | |
| 2007/0055254 A1 | 3/2007 | Ihde | |
| 2007/0083087 A1 | 4/2007 | Carda | |
| 2007/0085496 A1 | 4/2007 | Philipp et al. | |
| 2007/0225704 A1 | 9/2007 | Ziran et al. | |
| 2007/0233134 A1 | 10/2007 | Bastian et al. | |
| 2008/0021451 A1 | 1/2008 | Coull et al. | |
| 2009/0036890 A1 | 2/2009 | Karidis | |
| 2009/0036892 A1 * | 2/2009 | Karidis | A61B 17/66 606/60 |
| 2010/0087819 A1 | 4/2010 | Mullaney | |
| 2010/0262160 A1 | 10/2010 | Boyden et al. | |
| 2010/0262239 A1 | 10/2010 | Boyden et al. | |
| 2010/0305568 A1 | 12/2010 | Ross et al. | |
| 2010/0312243 A1 | 12/2010 | Ross et al. | |
| 2010/0331840 A1 | 12/2010 | Ross et al. | |
| 2011/0004199 A1 | 1/2011 | Ross et al. | |
| 2011/0118738 A1 | 5/2011 | Vasta et al. | |
| 2011/0166572 A1 | 7/2011 | Ihde | |
| 2011/0313418 A1 | 12/2011 | Nikonovas | |
| 2011/0313419 A1 | 12/2011 | Mullaney | |
| 2012/0041439 A1 | 2/2012 | Singh et al. | |
| 2012/0130384 A1 | 5/2012 | Henderson | |
| 2012/0303028 A1 | 11/2012 | Wong | |
| 2012/0303029 A1 | 11/2012 | Vasta et al. | |
| 2013/0018374 A1 | 1/2013 | Edelhauser et al. | |

FOREIGN PATENT DOCUMENTS

| | | |
|---|---|---|
| DE | 9316164 U1 | 7/1994 |
| DE | 4421223 A1 | 12/1995 |
| DE | 102007026404 A1 | 12/2008 |
| EP | 0029298 A1 | 5/1981 |
| EP | 1239784 B1 | 4/2006 |
| EP | 1916952 B1 | 12/2009 |
| EP | 2134515 B1 | 7/2010 |
| EP | 2417923 A1 | 2/2012 |
| GB | 421788 | 12/1934 |
| GB | 2229096 A | 9/1990 |
| IT | 1259768 B | 3/1996 |
| JP | S52-003290 | 8/1978 |
| JP | S63-500499 | 2/1988 |
| JP | H02180254 A | 7/1990 |
| JP | H10290807 A | 11/1998 |
| JP | 2003508108 A | 3/2003 |
| JP | 2003508150 A | 3/2003 |
| JP | 2005-137586 | 6/2005 |
| WO | 9222268 A1 | 12/1992 |
| WO | 9626678 A1 | 9/1996 |
| WO | 9730650 A1 | 8/1997 |
| WO | 9812975 A2 | 4/1998 |
| WO | 9815231 A1 | 4/1998 |
| WO | 9920193 A1 | 4/1999 |
| WO | 9947060 A1 | 9/1999 |
| WO | 9948414 A2 | 9/1999 |
| WO | 0003647 A1 | 1/2000 |
| WO | 0115611 A1 | 3/2001 |
| WO | 0122892 A1 | 4/2001 |
| WO | 03086211 A1 | 10/2003 |
| WO | 03086212 A2 | 10/2003 |
| WO | 03086213 A2 | 10/2003 |
| WO | 2004026103 A2 | 4/2004 |
| WO | 2007002180 A2 | 1/2007 |
| WO | 2007060507 A2 | 5/2007 |
| WO | 2007139031 A1 | 12/2007 |
| WO | 2008002992 A1 | 1/2008 |
| WO | 2008134624 A1 | 11/2008 |
| WO | 2009018349 A2 | 2/2009 |
| WO | 2009018398 A2 | 2/2009 |
| WO | 2009100247 A1 | 8/2009 |
| WO | 2009100459 A1 | 8/2009 |
| WO | 2009102904 A1 | 8/2009 |
| WO | 2009105479 A1 | 8/2009 |
| WO | 2010042619 A1 | 4/2010 |
| WO | 2010104567 A1 | 9/2010 |
| WO | 2010120367 A1 | 10/2010 |
| WO | 2011017321 A2 | 2/2011 |
| WO | 2011060264 A1 | 5/2011 |
| WO | 2011060266 A1 | 5/2011 |
| WO | 2011106507 A1 | 9/2011 |
| WO | 2011146703 A1 | 11/2011 |
| WO | 2011163406 A2 | 12/2011 |

OTHER PUBLICATIONS

Japanese Office Action, dated Nov. 26, 2013, JP Application No. 2010-545284, 4 pages.
International Search Report and Written Opinion, PCT/US2013/064067, dated Jan. 31, 2014, 7 pages.
International Search Report and Written Opinion, PCT/RU2013/000203, dated Jan. 29, 2014, 23 pages.
Canero, C., et al., "Predictive (Un)distortion Model and 3-D Reconstruction by Biplane Snakes, IEEE Transactions on Medical Imaging," vol. 21, No. 9, (Sep. 2002), 14 pages.
Ghanem, R.N., et al., "Heart-Surface Reconstruction and ECG Electrodes Localization Using Fluoroscopy, Epipolar Geometry and Stereovision: Application to Noninvasive Imaging of Cardiac Electrical Activity," IEEE Transactions on Medical Imaging, vol. 22, No. 10, (Oct. 2003), 12 pages.

(56) References Cited

OTHER PUBLICATIONS

Li, Y., et al., "Distortion Correction and Geometric Calibration for X-Ray Angiography System," IEEE Transactions on Nuclear Science, vol. 56, No. 3, (Jun. 2009), 12 pages.

Selby, B.P., et al., "Patient positioning with X-ray detector self-calibration for image guided therapy," Australas Phys. Eng. Sci. Med., vol. 34, (2011), 10 pages.

Yang, J., et al., "Novel Approach for 3-D Reconstruction of Coronary Arteries From Two Uncalibrated Angiographic Images," IEEE Transactions on Image Processing, vol. 18, No. 7, (Jul. 2009), 10 pages.

Zheng, G., et al., "A 2D/3D correspondence building method for reconstruction of a patient-specific 3D bone surface model using point distribution models and calibrated X-ray images," Medical Image Analysis, vol. 13, (2009), 17 pages.

European Extended Search Report, EP Application No. 09710983.9-1654 / 2249721 PCT/US2009/033975, dated Apr. 4, 2014, 7 pages.

International Search Report, PCT/US2009/034413, dated Apr. 15, 2009, 1 page.

International Preliminary Report on Patentability, PCT/US2009/034413, dated Aug. 24, 2010, 7 pages.

Extended European Search Report, Application No. 09712412.7-1526, PCT/US2009/034413, dated Dec. 3, 2012, 10 pages.

International Search Report, PCT/US2010/056541, dated Jan. 12, 2011, 1 page.

International Preliminary Report on Patentability, PCT/US2010/056541, Date of issuance May 15, 2012, 7 pages.

International Preliminary Report on Patentability, PCT/US2010/056539, Date of issuance May 15, 2012, 9 pages.

International Search Report, PCT/US2010/056539, Dated Jan. 18, 2011, 2 pages.

Steffen Schumann, et al., "Calibration of X-ray radiographs and its feasible application for 2D/3D reconstruction of the proximal femur" (2008), 4 pages.

Jetzki S., et al., "Fluoroscopy-Based 3-D Reconstruction of Femoral Bone Cement: A New Approach for Revision Total Hip Replacement," (2005), 12 pages.

Guoyan Zheng, et al., "3-D reconstruction of a surface model of the proximal femur from digital biplanar radiographs," (2008), 4 pages.

Laporte S., et al., "A biplanar reconstruction method based on 2D and 3D contours: application to the distal femur," (2003), 6 pages.

Japanese Office Action, JP Application No. 2010-546960, dated Mar. 12, 2013, 4 pages.

Japanese Office Action, JP Application No. 2010-546904, dated Mar. 12, 2013, 6 pages.

Japanese Office Action, JP Application No. 2010-546098, dated Mar. 5, 2013, 11 pages.

International Preliminary Report on Patentability, PCT/RU2010/000452, dated Feb. 26, 2013, 9 pages.

Japanese Office Action, JP Application No. 2010-545284, dated Mar. 5, 2013, 6 pages.

European Extended Search Report, Application No. 09707791.1-1654 / 2240084, PCT/US2009/033258, dated Nov. 21, 2013, 6 pages.

Japanese office action, JP Application No. 2010-546904, dated Oct. 29, 2013, 4 pages.

\* cited by examiner

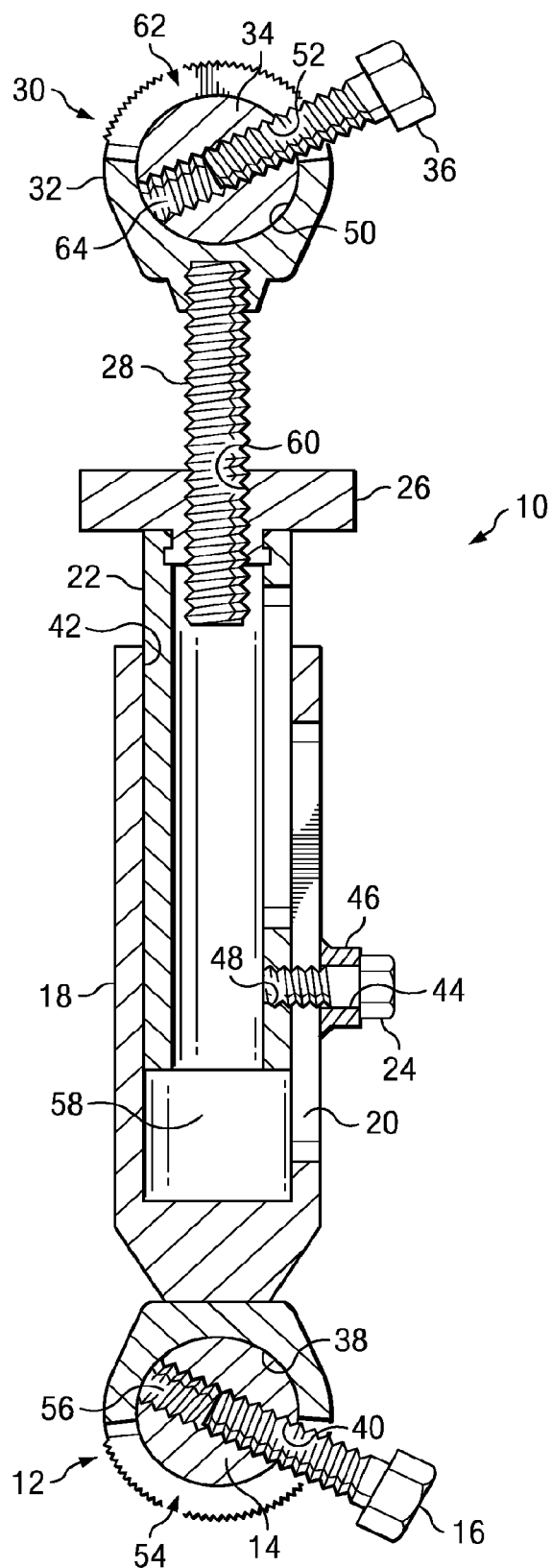
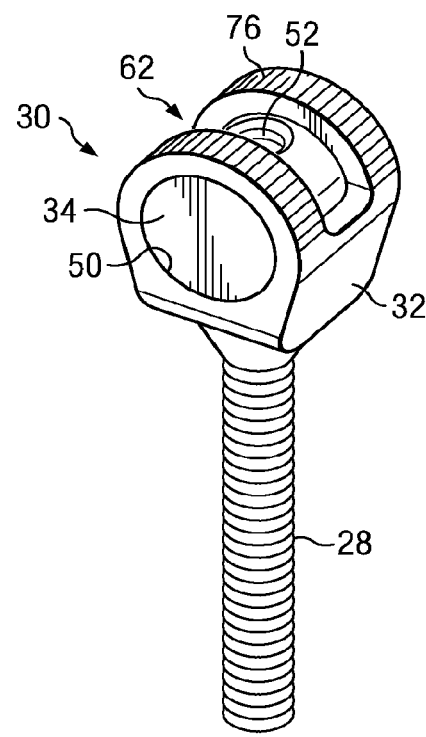
FIG. 3
FIG. 4

EXTERNAL FIXATION CONNECTION ROD FOR RAPID AND GRADUAL ADJUSTMENT

This is a continuation application of U.S. application Ser. No. 13/675,961, which was filed on Nov. 13, 2012, the entirety of which is hereby incorporated by reference.

TECHNICAL FIELD

The present disclosure relates in general to the field of external fixation, and more specifically, to connection rods having an adjustment mechanism that allows for both rapid and gradual adjustment of an overall length of the connection rods.

BACKGROUND

Without limiting the scope of the disclosure, this background section is described in connection with external fixation devices and specifically connection rods. Generally, external fixation devices are commonly used in a variety of surgical procedures including limb lengthening, deformity correction, fracture reduction and treatment of non-unions, mal-unions and bone defects. The process involves a rigid framework comprising several rings that are placed externally around the limb and attached to bone segments using wires and half pins inserted into the bone segments and connected to the related section of the external rigid framework. The opposite rings of the rigid framework are interconnected by either threaded or telescopic rods directly or in conjunction with uni-planar or multi-planar hinges, which allow the surgeon to connect opposite rings that are not parallel to each other after manipulation with bone segments either rapidly (acutely) or gradually over a period of time.

For example, in bone fracture reduction or non-union treatment, the wires and half pins are inserted into each bone segment and attached to rings of a rigid framework. The rigid framework is used to acutely reduce a displacement and restore alignment between the bone segments. During the realignment of the bone segments, the orientations of opposite rings often are not parallel. Those opposite rings of the rigid framework are connected together by threaded or telescopic rods with attached uni-planar or multi-planar hinges. This allows the opposite bone segment to be rigidly fixed until complete fracture healing or bone consolidation is completed.

SUMMARY

The present enclosure includes embodiments of a external fixation connection rod that allows for rapid, coarse adjustments of the rod length and is operable to be easily and rigidly attached to non-parallel external fixator rings.

In one embodiment the present invention includes a connecting rod for an external fixation device, the connecting rod defining a longitudinal axis and comprising: a telescopic housing comprising a housing body having an axial bore defined therethrough; an inner sleeve slidably disposed within the axial bore of the telescopic housing, the inner sleeve and the telescopic housing being releasably coupled by a fastener, the inner sleeve comprising: a sleeve body having an axial bore defined therethrough; an indexing flange coupled to a distal end of the sleeve body; and a tip coupled to a distal surface of the indexing flange; an adjustment mechanism disposed about the tip of the inner sleeve, the adjustment mechanism comprising: a first rotating member having an axial bore defined therethrough, the axial bore comprising: a polygonal recess in a distal end; and an inner recess in a proximal end operable to receive the indexing flange of the inner sleeve; a second rotating member having a threaded axial bore defined therethrough, the second rotating member comprising: a polygonal head at a distal end operable to mate with the polygonal recess of the first rotating member; and a proximal portion comprising an inner recess operable to receive the tip of the inner sleeve; a biasing member placed adjacent to the proximal portion of the second rotating member; and an externally threaded elongated member threadably coupled within the second rotating member of the adjustment mechanism; wherein in a first, locked position, the inner recess of the proximal end of the first rotating member receives the indexing flange of the inner sleeve, thereby preventing the adjustment mechanism from rotating about the inner sleeve and the elongated member; wherein in a second, unlocked position, the first rotating member is distally translated relative to the second rotating member and the inner recess of the proximal end of the first rotating member disengages from the indexing flange of the inner sleeve, thereby allowing the adjustment mechanism to rotate about the inner sleeve and the elongated member; wherein when the adjustment mechanism is rotated about the inner sleeve and the elongated member, the elongated member is translated within the axial bore defined in the inner sleeve during gradual adjustment, thereby lengthening or shortening an overall length of the connecting rod; and wherein when the adjustment mechanism is rotated about the inner sleeve and the elongated member, the adjustment mechanism is biased by the biasing member to return to the first, locked position when the inner recess of the proximal end of the first rotating member aligns with and receives the indexing flange of the inner sleeve.

Another embodiment of the present invention includes a connecting rod adjustment mechanism comprising: a first rotating member having an axial bore defined therethrough, the axial bore comprising: a recess in a distal end; and an inner recess in a proximal end operable to receive an indexing flange of the inner sleeve; a second rotating member having a threaded axial bore defined therethrough, the second rotating member comprising: an indexing head shaped at a distal end operable to mate with the recess of the first rotating member, wherein the shape to allow the adjustment mechanism to rotate about the inner sleeve and the elongated member; wherein when the adjustment mechanism is rotated about the inner sleeve and the elongated member, the elongated member is translated within the axial bore defined in the inner sleeve during gradual adjustment, thereby lengthening or shortening an overall length of the connecting rod; and wherein when the adjustment mechanism is rotated about the inner sleeve and the elongated member, the adjustment mechanism is biased by the biasing member to return to the first, locked position when the inner recess of the proximal end of the first rotating member aligns with and receives the indexing flange of the inner sleeve after.

In one aspect, the fastener is loosened, the inner sleeve can slidably translate within the axial bore of the telescopic housing during rapid adjustment, thereby lengthening or shortening the overall length of the connecting rod. In another aspect, the telescopic housing comprises a first joint coupled to a proximal end portion of the housing body, and a first rotating member received in the first joint, wherein the first rotating member comprises a first connection mechanism operable to releasably couple the first rotating member to a first ring. In another aspect, the externally threaded elongated member comprising a second joint coupled to a distal end portion of the threaded rod, and a second rotating member received in the second joint, wherein the second rotating member comprises a second connection mechanism operable to releasably couple the second rotating member to a second ring. In another aspect, the biasing member is a spring, a leaf spring, a clip, a coil spring, a wave spring, a linear rate spring, a progressive rate spring, a dual rate spring, a flat spring, a conical spring, or a compression spring. In another aspect, when the outer circumference of the indexing flange is substantially similar in shape to an inner sidewall of the inner recess of the proximal end of the first rotating member, this allows the inner recess to receive the indexing flange in the first, locked position. In another aspect, the outer circumference of the indexing flange comprises two opposing flat sides separated by two round portions.

In another aspect, the inner sidewall of the inner recess of the proximal end of the first rotating member comprises two opposing flat sides separated by two round portions. In another aspect, the adjustment mechanism is in its second, unlocked position, the first rotation member and the second rotation member are operable to rotate 180° until the spring bias of the spring returns the adjustment mechanism to the first, locked position, thereby lengthening or shortening the overall length of the connecting rod. In another aspect, the first rotation member further comprises an inwardly extending flange distal to the inner recess of the proximal end. In another aspect, the spring compresses between a distal side of the inwardly extending flange of the first rotation member and a proximal side of the head of the second rotation member when the first compression member is translated from the first, locked position to the second, unlocked position. In another aspect, the tip of the inner sleeve further comprises a plurality of mating barbs about an outer circumference of the tip.

Yet another embodiment of the present invention also includes a method of adjusting the position of first and second external fixation devices, comprising: providing a connecting rod having a longitudinal axis and comprising: a telescopic housing comprising a housing body having an axial bore defined therethrough; an inner sleeve slidably disposed within the axial bore of the telescopic housing, the inner sleeve and the telescopic housing being releasably coupled by a fastener, the inner sleeve comprising: a sleeve body having an axial bore defined therethrough; an indexing flange coupled to a distal end of the sleeve body; and a tip coupled to a distal surface of the indexing flange; an adjustment mechanism disposed about the tip of the inner sleeve, the adjustment mechanism comprising: a first rotating member having an axial bore defined therethrough, the axial bore comprising: a polygonal recess in a distal end; and an inner recess in a proximal end operable to receive the indexing flange of the inner sleeve; a second rotating member having a threaded axial bore defined therethrough, the second rotating member comprising: a polygonal head at a distal end operable to mate with the polygonal recess of the first rotating member; and a proximal portion comprising an inner recess operable to receive the tip of the inner sleeve; a biasing member placed adjacent to the proximal portion of the second rotating member; and an externally threaded elongated member threadably coupled within the second rotating member of the adjustment mechanism; receiving the indexing flange of the inner sleeve into the inner recess of the proximal end of the first rotating member, thereby preventing the adjustment mechanism from rotating about the inner sleeve and the elongated member in a first, locked position; translating the first rotating member relative to the second rotating member and the inner recess of the proximal end of the first rotating member along the longitudinal axis of the connecting rode and rotating the first rotating member about the inner sleeve, thereby disengaging the first rotating member from the indexing flange of the inner sleeve and allowing the adjustment mechanism to rotate about the inner sleeve and the elongated member in a second, unlocked position; rotating the adjustment mechanism about the inner sleeve and the elongated member, thereby translating the elongated member within the axial bore defined in the inner sleeve during gradual adjustment of an overall length of the connecting rod; and biasing the biasing member to return to the first, locked position when the adjustment mechanism is rotated about the inner sleeve and the elongated member and when the inner recess of the proximal end of the first rotating member aligns with and receives the indexing flange of the inner sleeve.

Described in one embodiment is a connecting rod for an external fixation device comprising a telescopic housing having a housing body having an axial bore defined therethrough; a first joint coupled to an end portion of the housing body; and a first rotating member received in the first joint, wherein the first rotating member is operable to rotate relative to the first joint about a first axis. The first rotating member comprises a first connection mechanism operable to releasably couple the first rotating member to a first fixator ring. The connecting rod further includes an adjustment sleeve slidably disposed within the axial bore, the adjustment sleeve and the telescopic housing being releasably coupled by a fastener, and an externally threaded elongated member threadably coupled the adjustment sleeve. The elongated member comprises a threaded rod; a second joint coupled to an end portion of the threaded rod; and a second rotating member received in the second joint, wherein the second rotating member is operable rotate relative to the second joint about a second axis. The second rotating member comprises a second connection mechanism operable to releasably couple the second rotating member to a second fixator ring. The first and second connection mechanisms are operable to substantially limit the rotational movement of the first and second rotating members, respectively.

In some embodiments the first and second connection mechanisms each comprise a fastener aperture defined in the first and second rotating member, respectively, and each fastener aperture is operable to receive a ring fastener disposed through a bore defined in the first or second ring.

In some embodiments, the first and second joints each comprise a socket, and the first and second rotating members comprise a first and second ball members, respectively, the first and second ball member being disposed in the socket of the first and second joints, respectively. In some exemplary embodiments, the sockets of first and second joints are seated in first and second seating members, respectively, and the seating members each have an inner recessed portion for receiving the socket of first or second joints, and an outer ring contact portion for providing a contact surface with the first or second ring.

In some particular embodiments, the first connection mechanism comprises a first connecting body extending radially from the first ball member, to the outside of the socket of the first joint, and through an aperture defined in the first seating member, and the first connecting body has a threaded portion operable to be inserted through a bore defined in the first ring. The second connection mechanism also comprises a second connecting body extending radially from the second ball member, to the outside of the socket of the second joint, and through an aperture defined in the second seating member, and the second connecting body has a threaded portion operable to be inserted through a bore defined in the second ring. In these embodiments, the threaded portions of the first and second connecting bodies each are operable to receive a mating nut.

The present disclosure also includes embodiments directed to a connecting rod for an external fixation device comprising a telescopic housing having a housing body, in which a first portion of the housing body comprises a first axial bore defined therethrough, and a second portion of the housing body comprises a second axial bore defined therethrough. The first and second axial bores have first and second longitudinal axes, respectively, and the first and second longitudinal axes are parallel and coplanar. The connecting rod further includes first and second sleeves slidably disposed within the first and second axial bores, respectively, and the first sleeve has an adjustment mechanism rotatably disposed on an end portion of the first sleeve. The connect rod further includes an elongated member threadably coupled to the adjustment mechanism such that rotating the adjustment mechanism causes the elongated member to translate along the first axis of the first axial bore. The housing body comprises first and second apertures defined in the walls of the first and second portions of the housing body, respectively, and the first and second apertures are aligned along the first and second axes, respectively. A first fastener is disposed through the first aperture of the housing body and received in a fastener aperture defined in the first sleeve, and a second fastener is disposed through the second aperture of the housing body and received in a fastener aperture defined in the second sleeve, the first and second fasteners being operable to releasably couple the first and second sleeves to the housing body, respectively.

The present disclosure also includes embodiments directed to fixation connection rod that allows for both rapid and gradual adjustment of an overall length of the fixation connection rod. The fixation connection rod may include an inner sleeve received within a telescopic rod to allow for rapid adjustment of the overall length of the fixation connection rod. The fixation connection rod may further include an adjustment mechanism to allow for gradual adjustment of the overall length of the fixation connection rod by lengthening or shortening a threaded elongated member received within a bore in the inner sleeve. The adjustment mechanism includes a first rotation member, a second rotation member, and a spring. Distal translation of the first rotation member relative to the second rotation member allows the adjustment mechanism to move from a first, locked position to a second, unlocked position, allowing the first rotation member and the second rotation member to rotate about the inner sleeve and the threaded elongated member during gradual adjustment, thereby lengthening or shorting the overall length of the fixation connection rod.

The present disclosure also includes embodiments for a method of maintaining the orientation of first and second fixator rings for immobilizing bone segments. One exemplary embodiment of the disclosed method includes providing a connecting rod comprising a telescopic housing having an axial bore defined therethrough; an adjustment sleeve slidably disposed within the axial bore, the adjustment sleeve and the telescopic housing; and an externally threaded elongated member threadably coupled to the adjustment sleeve. A first joint is coupled to an end portion of the housing, and a first rotating member is received in the first joint. Furthermore, the first rotating member comprises a first connection mechanism operable to releasably couple the first rotating member to the first fixator ring and substantially limit the rotational movement of the first rotating member. A second joint is coupled to an end portion of the housing, and a second rotating member is received in the second joint. Furthermore, the second rotating member comprises a second connection mechanism operable to releasably couple the second rotating member to the second fixator ring and substantially limit the rotational movement of the second rotating member. The disclosed embodiment further includes adjusting the longitudinal position of adjustment sleeve relative to the telescopic housing, and releasably coupling the adjustment sleeve to the telescopic housing using a sleeve fastener. The disclosed embodiment further includes using the first connection mechanism to releasably couple the first rotating member to the first fixator ring and substantially limit the rotational movement of the first rotating member, and using the second connection mechanism to releasably couple the second rotating member to the second fixator ring and substantially limit the rotational movement of the second rotating member.

BRIEF DESCRIPTION OF THE DRAWINGS

For a more complete understanding of the features and advantages of the present disclosure, reference is now made to the detailed description of the disclosure along with the accompanying figures in which:

FIG. 3 is a cutaway view of the external fixation connection rod of FIG. 1;

FIG. 4 is a perspective view of a portion of the external fixation connection rod of the present disclosure;

DETAILED DESCRIPTION

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not limit the scope of the disclosure.

To facilitate the understanding of this disclosure, a number of terms are defined below. Terms defined herein have meanings as commonly understood by a person of ordinary skill in the areas relevant to the present disclosure. Terms such as "a", "an" and "the" are not intended to refer to only a singular entity, but include the general class of which a specific example may be used for illustration. The terminology herein is used to describe specific embodiments of the disclosure, but their usage does not limit the disclosure, except as outlined in the claims.

The present disclosure includes embodiments directed to an external fixation connection rod with a housing that allows for rapid and gradual adjustment in length and having joint attachments to parallel or non-parallel rings or other external supports. The external fixation connection rod includes a telescopic housing having an axial bore defined therethrough. A first joint is coupled to an end portion of the housing body, and a first rotating member is received in the first joint. The first rotating member is operable to rotate relative to the first joint about a first axis, and comprises a first connection mechanism. The first connection mechanism releasably couples the first rotating member to a first fixator ring.

An adjustment sleeve is slidably disposed within the axial bore of the telescopic housing, and a sleeve fastener is used to secure the adjustment sleeve to the telescopic housing. The adjustment sleeve allows for coarse longitudinal length adjustments with respect to the telescopic housing. In some embodiments, the adjustment sleeve comprises an adjustment mechanism having a rotation element. The rotation element has an internally threaded bore defined therethrough, which allows for threaded connection to a threaded elongated member. The elongated member includes a threaded rod, and the external thread of the threaded rod and the internal thread of the threaded bore mate with each other such that rotating the rotation element causes the threaded elongated member to translate along a longitudinal axis of the connecting rod. Coupled to an end portion of the threaded rod is a second joint and a second rotating member received in the second joint. The second rotating member includes a second connection mechanism operable to releasably couple the second rotating member to a second fixator ring. Additionally, the first and second connection mechanisms are operable to substantially limit the rotational movement of the first and second rotating members, respectively.

Figure 1:
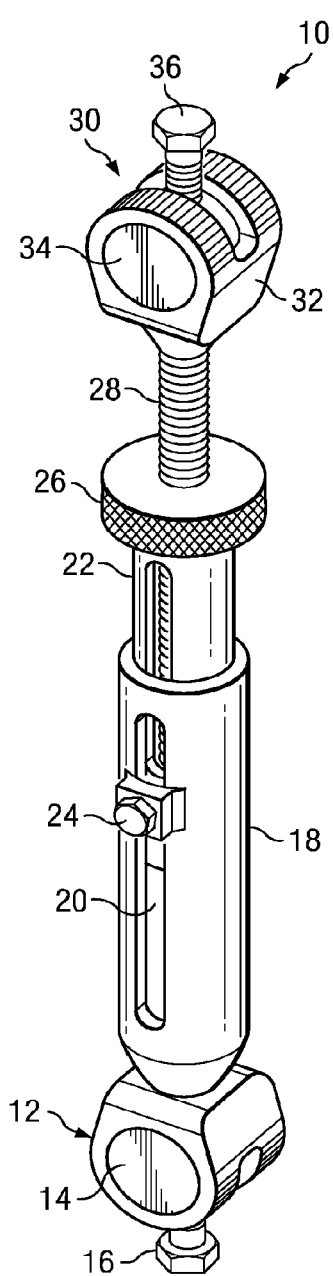
FIG. 1 is a perspective view of one embodiment of an external fixation connection rod of the present disclosure.

FIG. 1 is a perspective view of one embodiment of the external fixation connection rod of the present disclosure. The external fixation connection rod 10 includes a first articulatable joint 12 that houses a first rotating member 14. The first rotating member 14 includes a fastener 16 inserted into a fastener aperture defined (not shown) in the first rotating member 14 to secure the first articulatable joint 12 to an external fixator ring or other fixation device (not shown).

A telescopic housing 18 extends from the first articulatable joint 12 and has an axial bore (not shown) extending longitudinally from the first articulatable joint 12. The first articulatable joint 12 allows angular and rotational alignment of the telescopic housing 18. The telescopic housing 18 includes a telescopic housing adjustment aperture 20 in a wall of the telescopic housing. An adjustment sleeve 22 is positioned in the axial bore (not shown) of the telescopic housing 18. The adjustment sleeve 22 is slidable within the axial bore (not shown) to allow adjustment of the end-to-end length of the connecting rod 10 in a rapid manner. The adjustment sleeve 22 includes a sleeve fastener 24 disposed through the telescopic housing adjustment aperture 20 to secure the adjustment sleeve 22 to the telescopic housing 18.

An adjustment mechanism 26 is positioned at one end of the adjustment sleeve 22 and threadably connected to a threaded elongated member 28. The adjustment mechanism 26 adjusts longitudinally the threaded elongated member 28 to adjust the overall end-to-end length of the connecting rod 10 in a gradual manner. The threaded elongated member 28 includes a second articulatable joint 30 that includes a second articulatable joint housing 32 adapted to fit a second rotating member 34. The second rotating member 34 includes a second fastener 36 that is received in a fastener aperture (not shown) defined in the second rotating member 34 to secure the second articulatable joint 30 to an external fixator ring or other external support (not shown).

Figure 2:
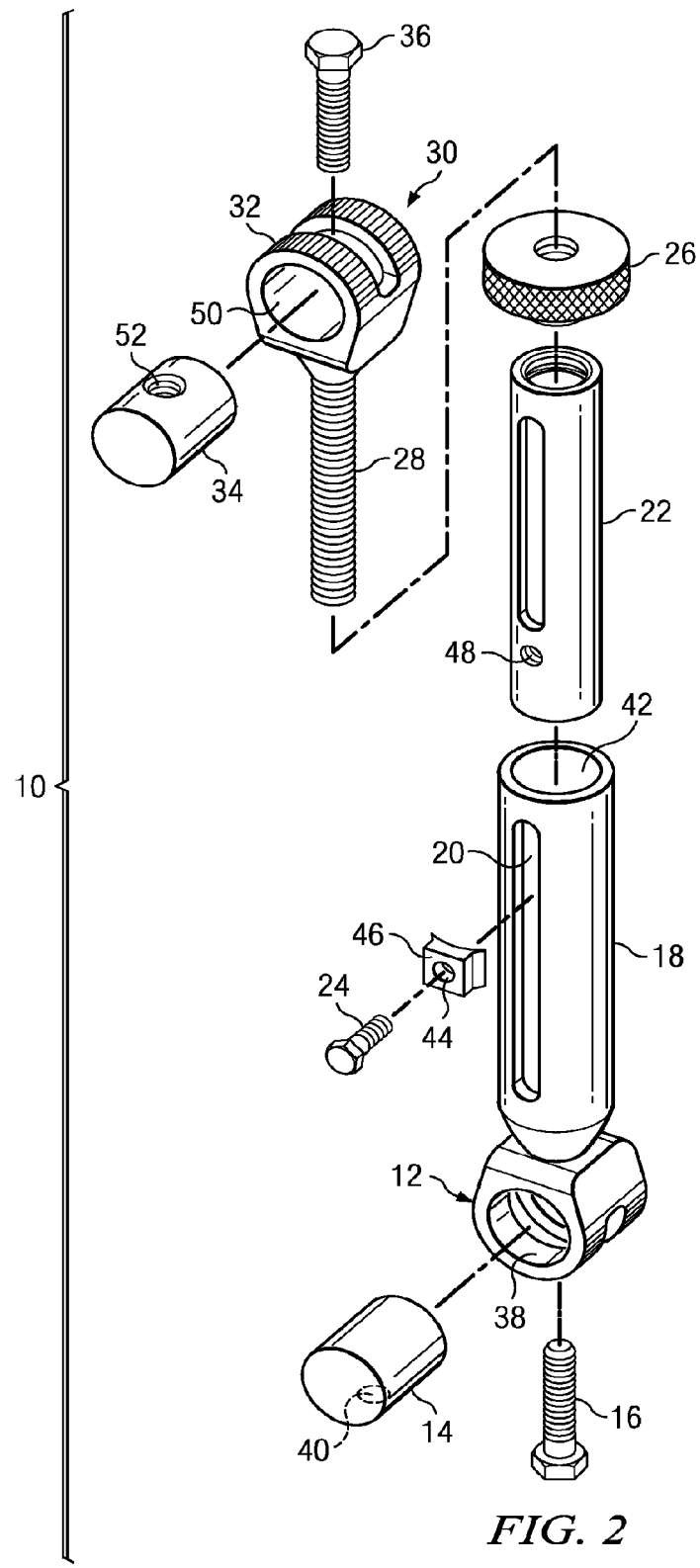
FIG. 2 is an exploded view of the external fixation connection rod of FIG. 1.

FIG. 2 is an exploded view of the embodiment shown in FIG. 1. The external fixation connection rod 10 includes a first articulatable joint 12 that houses a first rotating member 14. The first rotating member 14 passes through a joint aperture 38 that is sized and proportioned to fit the first rotating member 14. A fastener 16 passes through a slot (not shown) in the first articulatable joint 12 and into a fastener aperture 40 defined in the first rotating member 14 to secure the first articulatable joint 12 to an external fixator ring or other external 11 support (not shown). The first articulatable joint 12 allows angular and rotational alignment of the external fixation connection rod 10 relative to the first external fixator ring or other external support.

A telescopic housing 18 extends from the first articulatable joint 12 and has an axial bore (not shown) extending longitudinally from the first articulatable joint 12 to the axial bore aperture 42. The telescopic housing 18 includes a telescopic housing adjustment aperture 20. An adjustment sleeve 22 is slidably disposed within the axial bore (not shown) of the telescopic housing 18. The adjustment sleeve 22 is slidable within the axial bore (not shown) to allow adjustment of the end-to-end length of the external fixation connection rod 10 in a rapid manner. The adjustment sleeve 22 includes a sleeve fastener 24 that is inserted through a central opening 44 defined in a sleeve fastener washer 46 and through the telescopic housing adjustment aperture 20 into a sleeve fastener aperture 48 defined in the adjustment sleeve 22.

An adjustment mechanism 26 is rotatably coupled to an end portion of the adjustment sleeve 22 and threadably connected to a threaded elongated member 28. The adjustment mechanism is operable to rotate but not translate relative to the end portion of the adjustment sleeve 22. The adjustment mechanism 26 adjusts longitudinally the threaded elongated member 28 to adjust the overall end-to-end length of the external fixation connection rod 10 in a gradual manner.

The threaded elongated member 28 includes a second articulatable joint 30. The second articulatable joint 30 includes a second articulatable joint housing 32 adapted to fit a second rotating member 34. The second rotating member 34 passes through a second joint aperture 50 that is sized and proportioned to fit the second rotating member 34. A second fastener 36 disposed through a slot (not shown) in the second articulatable joint 30 and into a second fastener aperture 52 defined in the second rotating member 34 to secure the second articulatable joint 30 to an external fixator ring or other fixation device (not shown). The second articulatable joint 30 allows angular and rotational alignment of the external fixation connection rod 10 relative to the second external fixator ring (not shown) or other external support.

FIG. 3 is a cutaway view of the embodiment shown in FIGS. 1-2. The external fixation connection rod 10 includes a first articulatable joint 12 that houses a first rotating member 14. The first rotating member 14 passes through a joint aperture 38 that is sized and proportioned to fit the first rotating member 14. A fastener 16 is disposed through a slot 54 in the first articulatable joint 12 and fastener aperture 40 into a fastener aperture 56 defined in the first rotating member 14 to secure the first articulatable joint 12 to an external fixator ring or other external support (not shown). The first articulatable joint 12 allows angular and rotational alignment of the external fixation connection rod 10 relative to the first external fixator ring (not shown) or other external support.

A telescopic housing 18 extends from the first articulatable joint 12 and has an axial bore 58 extending longitudinally from the first articulatable joint 12 to the axial bore aperture 42. The telescopic housing 18 includes a telescopic housing adjustment aperture 20. An adjustment sleeve 22 is slidably disposed within the axial bore 58 of the telescopic housing 18. The adjustment sleeve 22 is slidable within the axial bore 58 to allow adjustment of the end-to-end length of the external fixation connection rod 10 in a rapid manner. The adjustment sleeve 22 includes a sleeve fastener 24 that is inserted through a sleeve fastener washer aperture 44 centrally defined in the sleeve fastener washer 46 and through the telescopic housing adjustment aperture (not shown) into a sleeve fastener aperture 48. Alternatively, the sleeve fastener 24 may include a separate sleeve washer 46 as a single unit.

An adjustment mechanism 26 is rotatably disposed at an end portion of the adjustment sleeve 22 and threadably connected to a threaded elongated member 28. In some embodiments, the adjustment mechanism 26 may include a rotation element, the rotation element having an internally threaded bore defined therethrough. The threaded elongated member 28 is disposed through the threaded bore 60 of the rotation element of the adjustment mechanism, and the external thread of the elongated member and the internal thread of the threaded bore mate with each other such that rotating the rotation element of the adjustment mechanism 26 causes the threaded elongated member 28 to translate along a longitudinal axis of the connecting rod. The adjustment mechanism 26 adjusts longitudinally the threaded elongated member 28 to adjust the overall end-to-end length of the external fixation connection rod 10 in a gradual manner. The threaded elongated member 28 includes a second articulatable joint 30.

The second articulatable joint 30 includes a second articulatable joint housing 32 adapted to fit a second rotating member 34. The second rotating member 34 passes through a second joint aperture 50 that is sized and proportioned to fit the second rotating member 34. A second fastener 36 is inserted through a slot 62 in the second articulatable joint 30 and a second fastner aperture 52 into a second threaded fastener bore 64 to secure the second articulatable joint 30 to an external fixator ring or other external support (not shown). The second articulatable joint 30 allows angular and rotational alignment of the external fixation connection rod 10 relative to the second external fixator ring (not shown) or other external support.

FIG. 4 is a perspective view of a portion of the external fixation connection rod of the present disclosure. The articulatable joint 30 includes an articulatable joint housing 32 adapted to fit a rotating member 34. The rotating member 34 passes through an articulatable joint aperture 50 that is sized and proportioned to fit the rotating member 34. A fastener (not shown) is inserted through a slot 62 in the articulatable joint 30 and a second fastner aperture 52 into a threaded fastener bore (not shown) to secure the articulatable joint 30 to an external fixator ring or other external support (not shown). The articulatable joint 30 may be textured 76 to provide increased adhesion or traction to the external fixator ring or other external supports (not shown).

Figure 5:
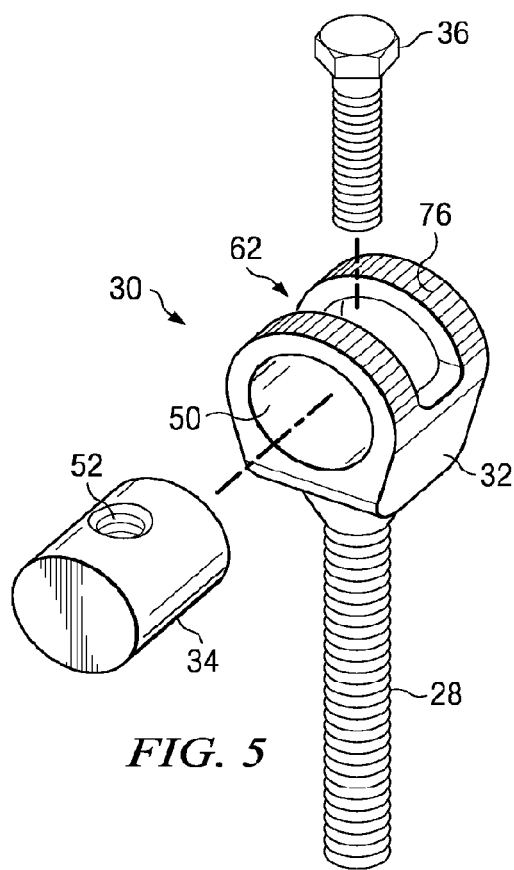
FIG. 5 is an exploded view of the portion of the external fixation connection rod of FIG. 4.

FIG. 5 is an exploded view of a portion of the external fixation connection rod of the present disclosure. The articulatable joint 30 includes an articulatable joint housing 32 adapted to fit a rotating member 34. The rotating member 34 passes through a joint aperture 50 that is sized and proportioned to fit the rotating member 34. A fastener 36 is inserted through a slot 62 in the articulatable joint 30 and a second fastner aperture 52 into a threaded fastener bore (not shown) to secure the articulatable joint 30 to an external fixator ring or other external support (not shown). The articulatable joint 30 may be textured 76 to provide increased adhesion or traction to the external fixator ring or other external supports (not shown).

Figure 6:
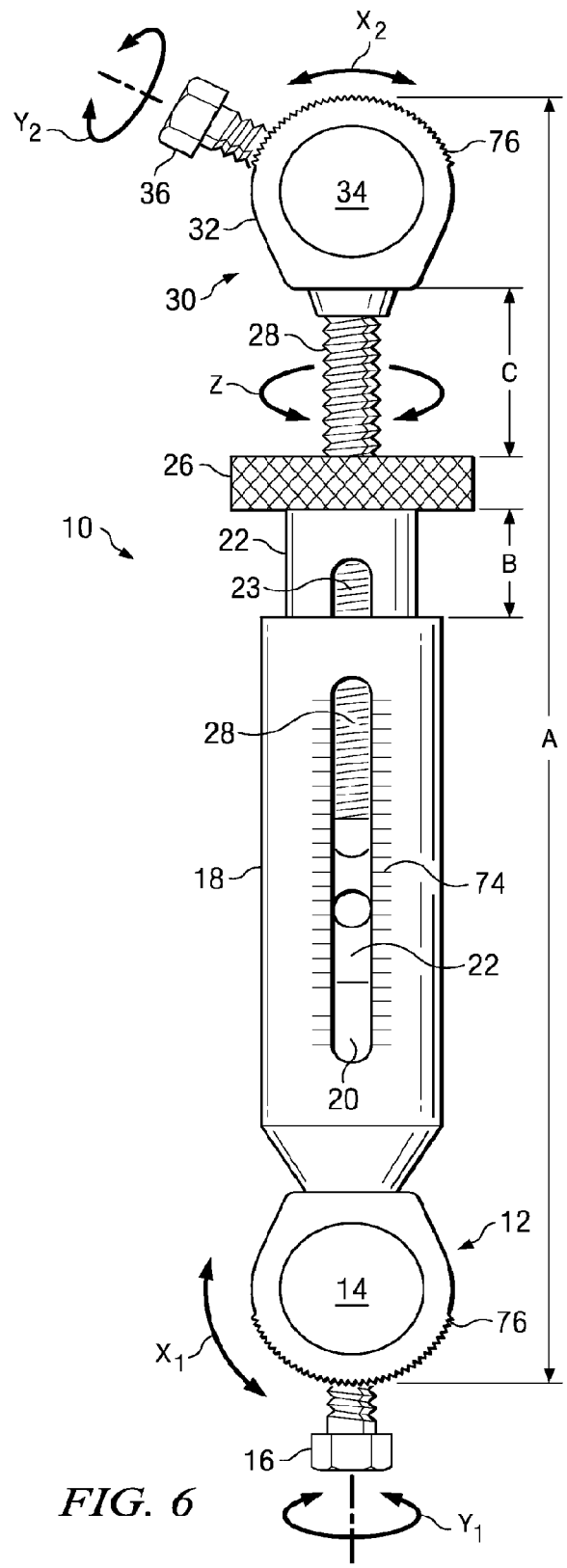
FIG. 6 is a side view of one embodiment of the external fixation connection rod of the present disclosure.

FIG. 6 is a side view of one embodiment of the external fixation connection rod of the present disclosure. The external fixation connection rod 10 includes a first articulatable joint 12 that houses a first rotating member 14. The first rotating member 14 includes a fastener 16 that is inserted through a slot (not shown) in the first articulatable joint 12 to secure the first articulatable joint 12 to an external fixator ring or other external support (not shown). The first articulatable joint 12 may be rotated about the X1 axis of the first rotating member 14 and around the Y1 axis of the fastener 16. This movement allows the first articulatable joint 12 to be secured by the fastener 16 at different angles relative to an external fixator ring or other fixation support (not shown).

A telescopic housing 18 extends from the first articulatable joint 12 and has an axial bore (not shown) extending longitudinally from the first articulatable joint 12. The telescopic housing 18 includes a telescopic housing adjustment aperture 20. An adjustment sleeve 22 is slidably disposed within the axial bore (not shown) of the telescopic housing 18. The adjustment sleeve 22 is slidable within the axial bore (not shown) to allow adjustment of the end-to-end length "A" of the external fixation connection rod 10 in a rapid manner. The movement of the adjustment sleeve 22 in the axial bore (not shown) of the telescopic housing 18 allows the distance "B" to be changed and in turn change the end-to-end length "A" of the external fixation connection rod 10.

The adjustment sleeve 22 includes a sleeve fastener (not shown) disposed through the telescopic housing adjustment aperture 20 to secure the adjustment sleeve 22 to the telescopic housing 18. The telescopic housing adjustment aperture 20 also serves as a window to allow positioning and referencing of the adjustment sleeve 22 and/or the threaded elongated member 28 to aid in the adjustment of the end-to-end length "A" of the external fixation connection rod 10 in a rapid manner.

An adjustment mechanism 26 is rotatably disposed at an end portion of the adjustment sleeve 22 and threadably connected to a threaded elongated member 28. The adjustment mechanism 26 may be rotated in direction "Z" to engage the threads of the threaded elongated member 28 and thereby adjust longitudinally the distance "C" and directly affect the end-to-end length "A" of the external fixation connection rod 10 in a gradual manner. The threaded elongated member 28 includes a second articulatable joint 30 that includes a second articulatable joint housing 32 adapted to fit a second rotating member 34. The second rotating member 34 includes a second fastener 36 that is inserted through a slot (not shown) in the second articulatable joint housing 32 to secure the second articulatable joint 30 to an external fixator ring or other external support (not shown).

The second articulatable joint 30 may be rotated about the X2 axis of the second rotating member 34 and around the Y2 axis of the second fastener 36. This movement allows the second articulatable joint 32 to be secured by the fastener 36 at different angles relative to an external fixator ring or other fixation support (not shown). It is not necessary for the first articulatable joint 12 be at the same angle, position or face relative to the second articulatable joint 30. In addition, the first articulatable joint 12, the second articulatable joint 30 or both articulatable joints 12 and 30 may be textured 76 to provide increased adhesion or traction to the external fixator ring or other external supports (not shown).

The graduation marks 74 may be calibrated into discrete increments (e.g., one millimeter increments) and may indicate the distance between the first articulatable joint 12 and the second articulatable joint 30 and relate to the end-to-end length "A" of the external fixation connection rod 10.

The graduation marks 74 indicate the lengths of the external fixation connection rod 10 as a relative value, rather than the distance from some predetermined specific length. The graduation marks do not necessarily have to be based on a traditional measuring system, or indicate the effective length of the strut at all. For instance, the graduation marks could indicate the percentage of total rod extension, or daily increments for cases where the translation takes place over an extended period of time. Reference to a neutral position can be useful to set the base members at a predetermined "neutral" position.

Figure 7:
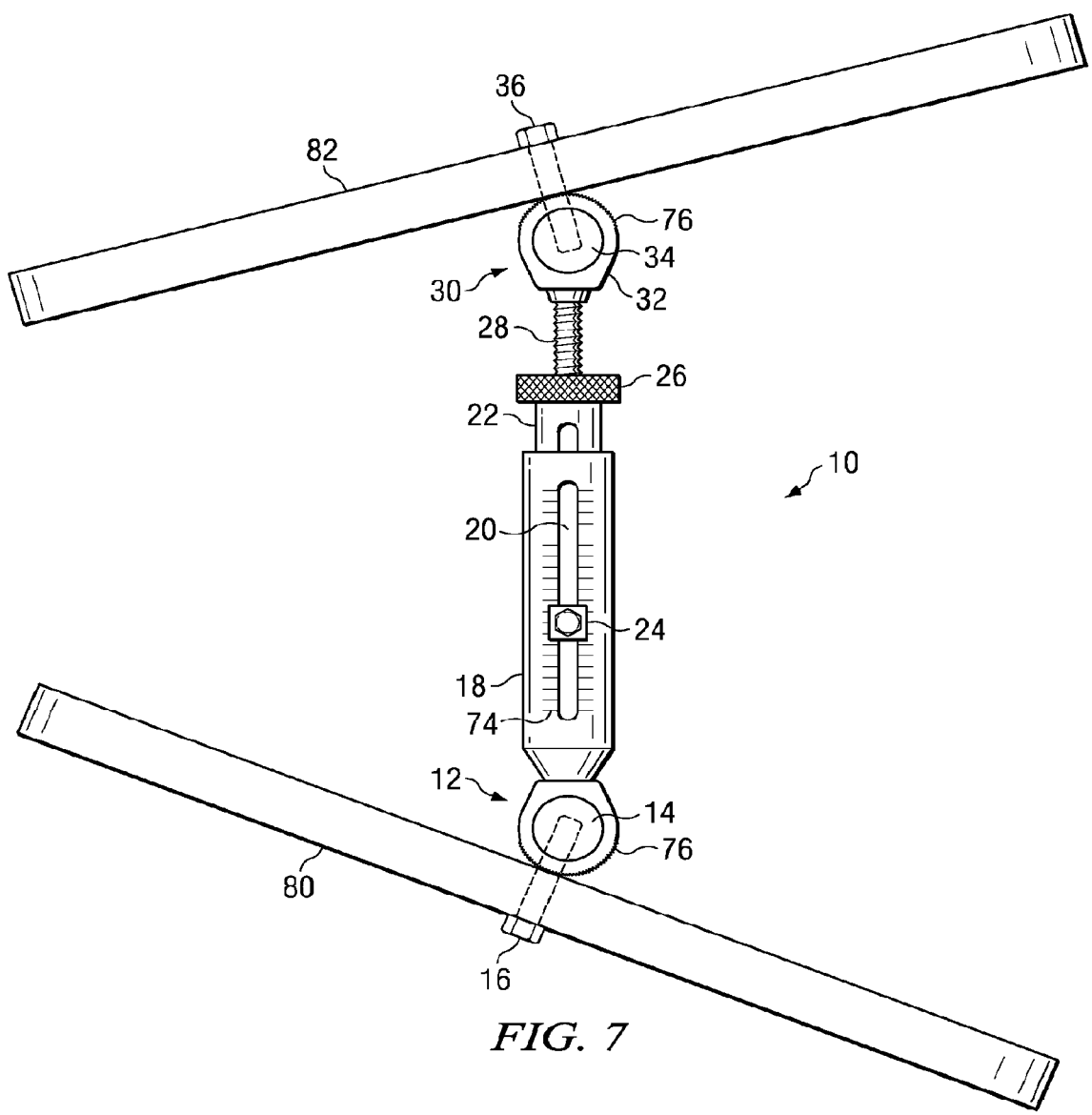
FIG. 7 is a side view of one embodiment of the external fixation connection rod of the present disclosure attached to an external fixation device.

FIG. 7 is a side view of one embodiment of the external fixation connection rod of the present disclosure attached to an external fixation device. An external fixation connection rod 10 is connected between a first external fixator ring 80 and a second external fixator ring 82. FIG. 7 depicts a single external fixation connection rod 10 disposed between the first external fixator ring 80 and the second external fixator ring 82 for simplicity sake. The skilled artisan will readily understand that numerous connecting rods 10 may be attached at various positions about the external fixator rings, that the angle of the external fixation connection rod 10 relative to the first external fixator ring 80 and the second external fixator ring 82 may be varied and the length of the external fixation connection rod 10 may be varied and adjusted.

A first articulatable joint 12 is secured to the external fixator ring 80 or other external support. The external fixation connection rod 10 includes a first articulatable joint 12 that houses a first rotating member 14. The first rotating member 14 includes a fastener 16 that passes through an aperture (not shown) defined in the first external fixator ring 80 and through a slot (not shown) in the first articulatable joint 12 to secure the first articulatable joint 12 to the external fixator ring 80 or other external support. The first rotating member 14 may be rotated to position the fastener 16 at different positions and in turn at different locations in the slot (not shown) of the first articulatable joint 12. This movement allows the first articulatable joint 12 to be secured at different angles relative to an external fixator ring 80 or other external support.

A telescopic housing 18 extends from the first articulatable joint 12 and has an axial bore (not shown) extending longitudinally from the first articulatable joint 12. The telescopic housing 18 includes a telescopic housing adjustment aperture 20. An adjustment sleeve 22 is slidably disposed within the axial bore (not shown) of the telescopic housing 18. The adjustment sleeve 22 is slidable within the bore (not shown) to allow adjustment of the end-to-end length "A" of the connecting rod 10 in a rapid manner.

The adjustment sleeve 22 includes a sleeve fastener 24 positioned through the telescopic housing adjustment aperture 20 to secure the adjustment sleeve 22 to the telescopic housing 18. The telescopic housing adjustment aperture 20 also serves as a window to allow positioning and referencing of the adjustment sleeve 22 and/or the threaded elongated member 28 to aid in the adjustment of the end-to-end length of the external fixation connection rod 10. The graduation marks 74 indicate the lengths of the external fixation connection rod 10 as a relative value, rather than the distance from some predetermined specific length. The graduation marks do not necessarily have to be based on a traditional measuring system, or indicate the effective length of the strut at all. For instance, the graduation marks could indicate the percentage of total rod extension, or daily increments for cases where the translation takes place over an extended period of time. Reference to a neutral position can be useful to set the base members at a predetermined "neutral" position.

An adjustment mechanism 26 is rotatably disposed at an end portion of the adjustment sleeve 22 and threadably connected to a threaded elongated member 28. The adjustment mechanism 26 may be rotated to engage the threads of the threaded elongated member 28 and thereby adjust longitudinally the end-to-end length of the connecting rod 10 in a gradual manner. The threaded elongated member 28 includes a second articulatable joint 30 with a second articulatable joint housing 32 adapted to fit a second rotating member 34. The second rotating member 34 includes a second fastener 36 that is inserted through an aperture (not shown) defined in the second external fixator ring 82 and into a slot (not shown) in the second articulatable joint housing 32 to secure the second articulatable joint 30 to an external fixator ring 82 or other external support.

The second articulatable joint 30 may be rotated to position the second fastener 36 at different positions and in turn at different locations in the slot of the second articulatable joint 30. This movement allows the second articulatable joint 30 to be secured at different angles relative to an external fixator ring 82 or other external support. It is not necessary for the first articulatable joint 12 be at the same angle, position or face relative to the second articulatable joint 30. In addition, the first articulatable joint 12, the second articulatable joint 30 or both articulatable joints 30 may be textured 76 to provide increased adhesion or traction to the external fixator ring 80 and 82 or other external supports.

Figure 8:
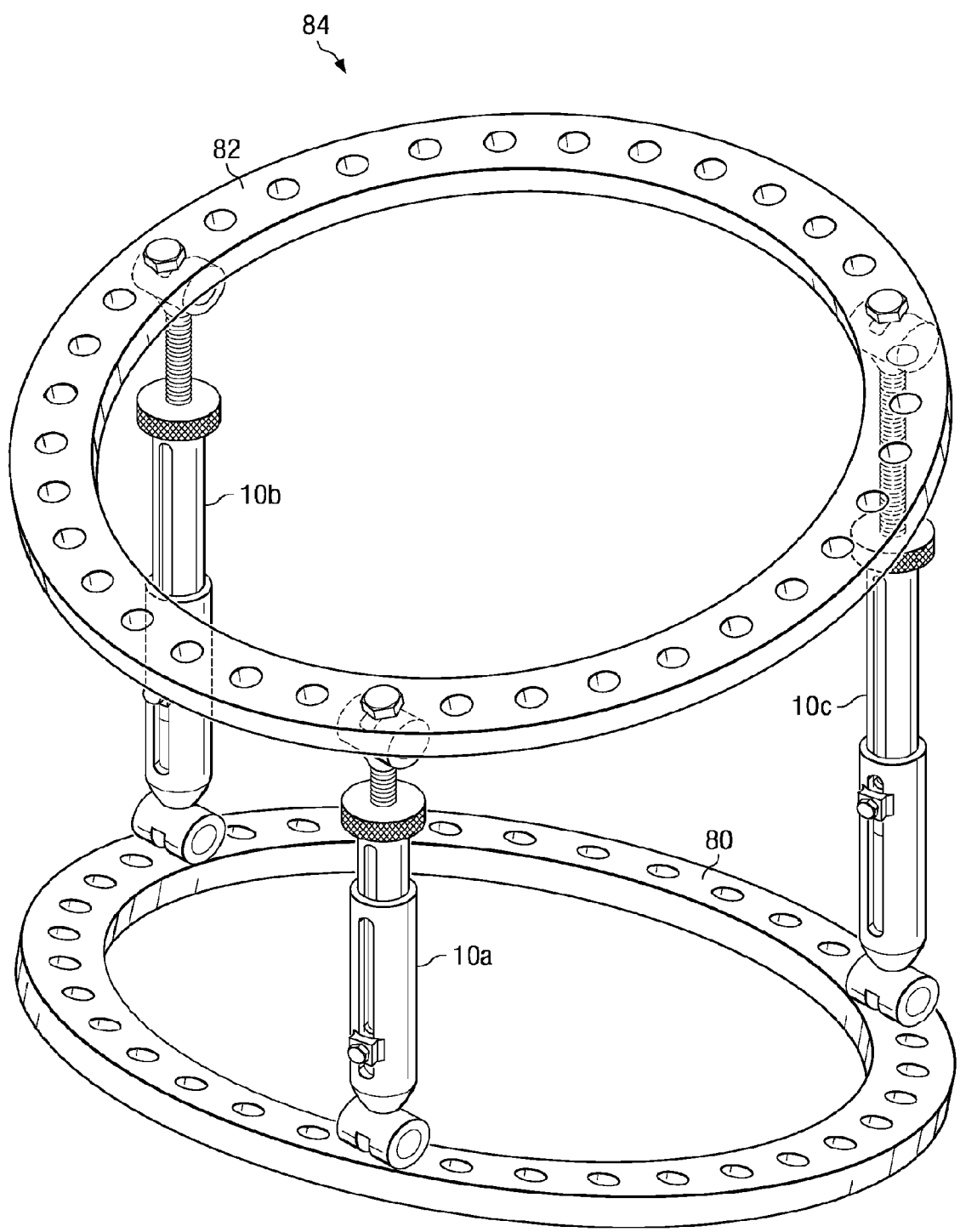
FIG. 8 is a perspective view of one embodiment of the external fixation connection rod of the present disclosure attached to an external fixation device.

FIG. 8 is a perspective view of one embodiment of the external fixation device using the external fixation connection rod of the present disclosure. The external fixation device 84 includes a first external fixator ring 80 and a second external fixator ring 82 connected by one or more external fixation connection rods 10. In this embodiment, there are three external fixation connection rods 10a, 10b, and 10c. Each of the external fixation connection rods (10a, 10b, and 10c) includes a first articulatable joint that houses a first rotating member. The first rotating member includes a fastener inserted through a slot (not shown) in the first articulatable joint to secure the first articulatable joint to an external fixator ring 80. In other embodiments, the external fixation connection rod 10 may be any connection rods described in this disclosure or constructed in accordance to the principles disclosed herein.

Figure 9:
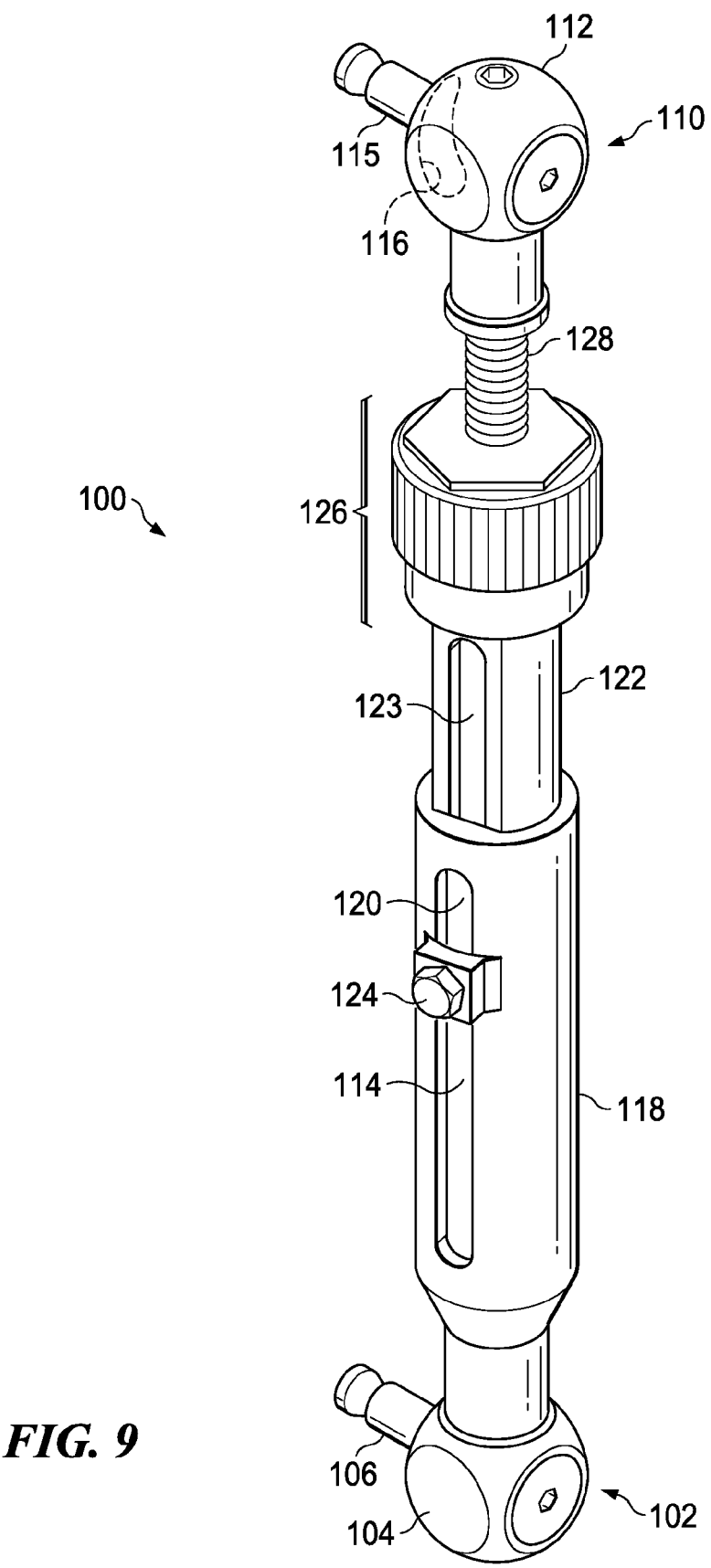
FIG. 9 is a perspective view of another embodiment of an external fixation connection rod of the present disclosure.

Referring to FIGS. 9-13, another embodiment of an external fixation connection rod 100 is shown. FIG. 9 depicts the external fixation connection rod 100 including a first articulatable joint 102 that includes a first articulatable joint housing 104 operable to receive a first fastener 106. The first fastener 106 may be used to secure the first articulatable joint 102 to a first external fixator ring or other fixation device (not shown). The first fastener 106 may articulate within a channel (not shown) defined in the first articulatable joint housing 104.

An outer telescopic housing 118 extends from the first articulatable joint 102 and includes an axial bore 114 defined within and extending longitudinally from the first articulatable joint 102. The first articulatable joint 102 allows angular and rotational alignment of the outer telescopic housing 118. The outer telescopic housing 118 includes a telescopic housing adjustment aperture 120 in a wall of the outer telescopic housing 118. An inner adjustment sleeve 122 is operable to be received within the axial bore 114 of the outer telescopic housing 118. The inner adjustment sleeve 122 is slidable within the axial bore 114 to allow adjustment of the end-to-end length of the external fixation connection rod 100 in a rapid manner. The inner adjustment sleeve 122 also includes an axial bore 123 defined within. A sleeve fastener 124 is operable to be disposed through the telescopic housing adjustment aperture 120 to secure the inner adjustment sleeve 122 to the outer telescopic housing 118. In an embodiment, the sleeve fastener 124 may comprise a side locking bolt and a clamp washer (not shown).

An adjustment mechanism 126 is connected to one end of the adjustment sleeve 122. A threaded elongated member 128 is threadably disposed within the adjustment mechanism 126. In an embodiment, the threaded elongated member 128 is a threaded rod. The adjustment mechanism 126 is operable to translate the threaded elongated member 128 with a matching thread, thereby more gradually adjusting the overall end-to-end length of the external fixation connection rod 100 than rapid adjustment of the inner adjustment sleeve 122 relative to the outer telescopic housing 118.

The threaded elongated member 128 includes a second articulatable joint 110 at a distal end that includes a second articulatable joint housing 112. The second articulatable joint 110 includes a second fastener 115 that may be used to secure the second articulatable joint 110 to a second external fixator ring or other external support (not shown). The second fastener 115 may articulate within a channel 116 defined in the second articulatable joint housing 112.

Figure 10:
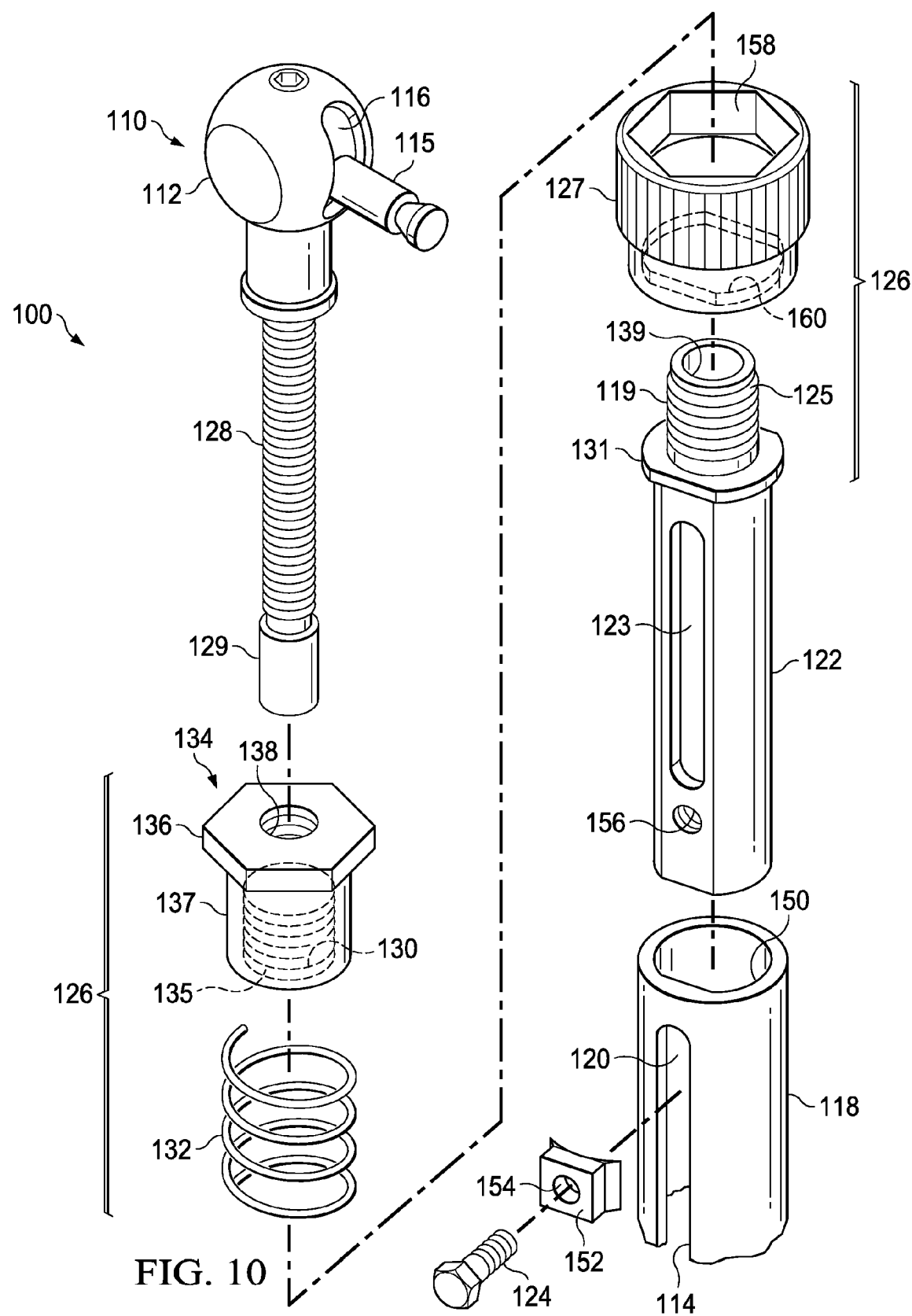
FIG. 10 is an exploded view of an adjustment mechanism portion of the external fixation connection rod of FIG. 9.
Figure 11:
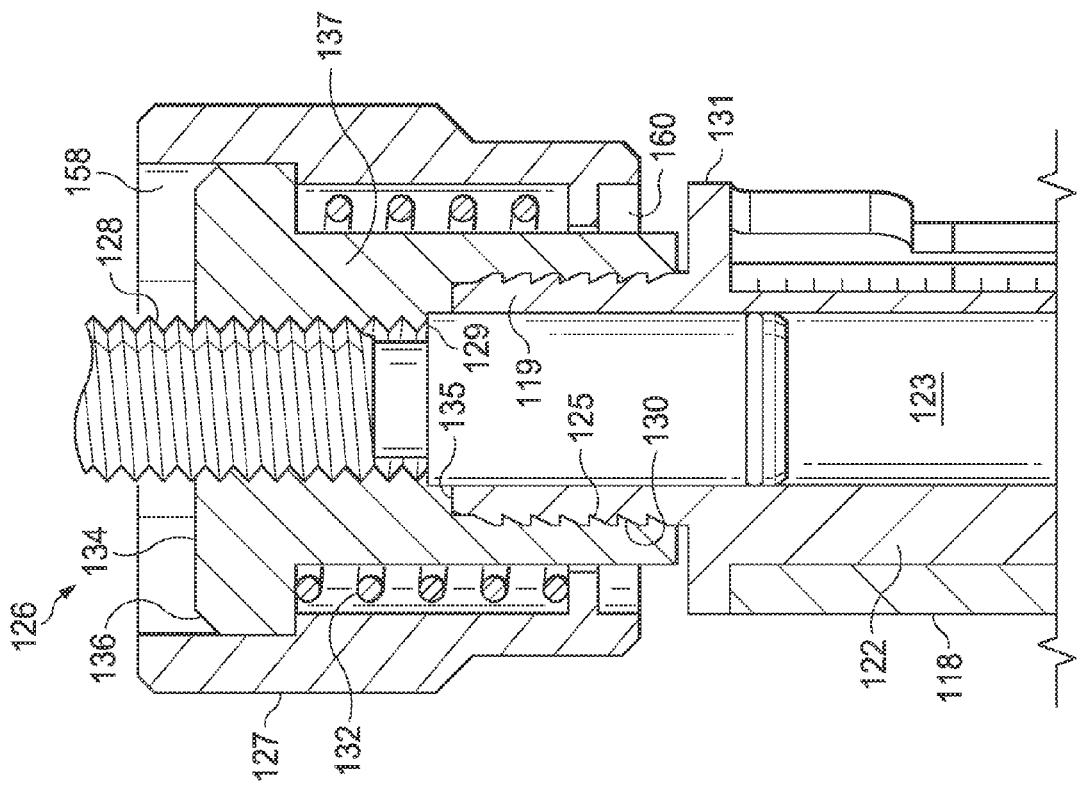
FIG. 11 is a cross-sectional view of the adjustment mechanism portion of the external fixation connection rod of FIG. 10 in a first, locked position.
Figure 12:
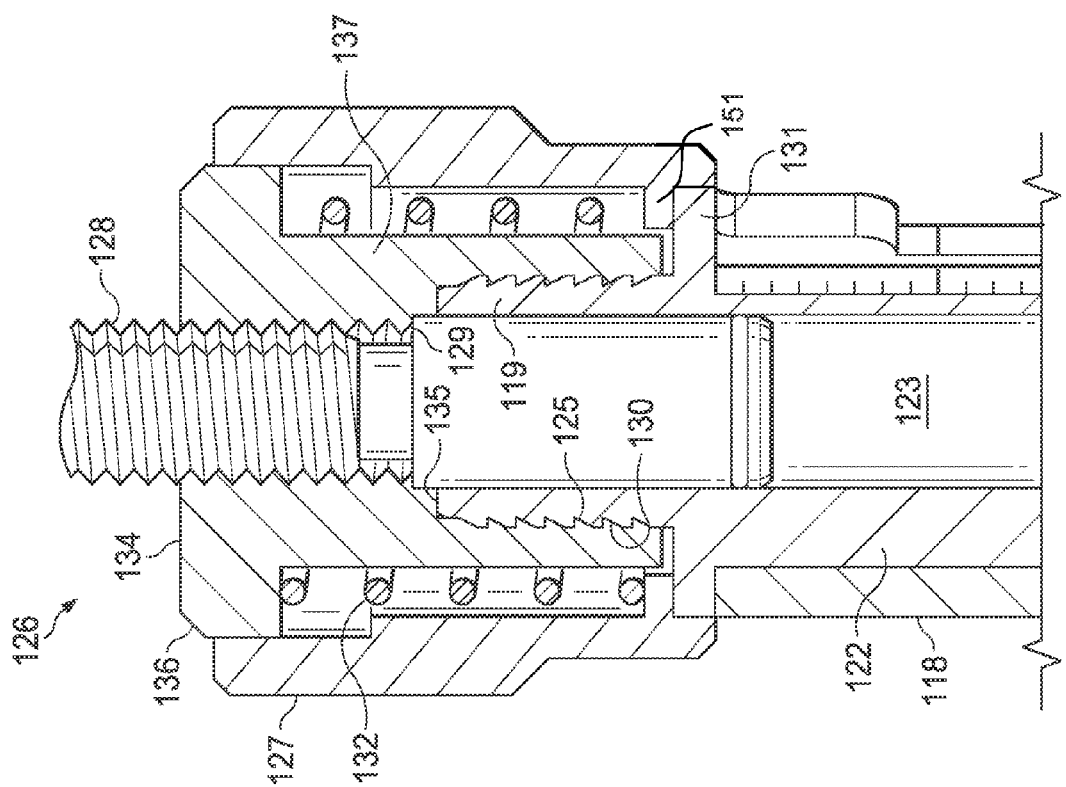
FIG. 12 is a cross-sectional view of the adjustment mechanism portion of the external fixation connection rod of FIG. 10 in a second, unlocked position.

FIG. 10 is an exploded view of the adjustment mechanism 126 portion of the external fixation connection rod 100 of FIG. 9. FIG. 11 is a cross-sectional view of the adjustment mechanism 126 portion of the external fixation connection rod 100 of FIG. 10 in a first, locked position. FIG. 12 is a cross-sectional view of the adjustment mechanism 126 portion of the external fixation connection rod 100 of FIG. 10 in a second, unlocked position.

As shown in FIGS. 10-12, the external fixation connection rod 100 includes the outer telescopic housing 118 extending from the first articulatable joint (not shown) to an axial bore aperture 150. The outer telescopic housing 118 includes the telescopic housing adjustment aperture 120. The inner adjustment sleeve 122 is slidably disposed within the axial bore aperture 150 to allow adjustment of the end-to-end length of the external fixation connection rod 100 in a rapid manner. The inner adjustment sleeve 122 includes the sleeve fastener 124 that is inserted through a central opening 154 defined in a sleeve fastener washer 152, through the telescopic housing adjustment aperture 120, and into a sleeve fastener aperture 156 defined in a proximal portion of the inner adjustment sleeve 122. Opposite the sleeve fastener aperture 156, a distal end of the adjustment sleeve 122 includes an indexing flange 131 and a tip 119 that includes circumferential mating barbs 125. According to one embodiment, a circumference of the indexing flange 131 is generally round in shape with two flat sides approximately 180° from each other about the circumference. A diameter of the indexing flange 131 may be greater than a diameter of the inner adjustment sleeve 122, while a diameter of the tip 119 may be less than the diameter of the indexing flange 131. A distal end of the tip 119 may further include an internal recess 139 operable to receive the threaded elongated member 128 therethrough.

The adjustment mechanism 126 is coupled to the distal end of the inner adjustment sleeve 122. The adjustment mechanism 126 includes a first rotating member 127, a second rotating member 134, and in this embodiment a spring 132. The skilled artisan will recognize that spring 132 can be replaced with any resilient mechanism that allows the user to pull the first rotating member 127 distal from the inner adjustment sleeve 122 (in this embodiment) and once the necessary rotation and lengthening of the external fixation connection rod 100 is achieved, the first rotating member 127 returns to its original position. The resilient mechanism can be, for example, a spring, a leaf spring, a clip, a coil spring, a wave spring, a linear rate spring, a progressive rate spring, a dual rate spring, a flat spring, a conical spring, or a compression spring. The spring can be metal, plastic, polymeric, ferrous, or non-ferrous. In an embodiment, the first rotating member 127 may be a first locking collar. The first rotating member 127 may include a first outer diameter at a distal end and a second outer diameter at a proximal end, wherein the first outer diameter may be greater than the second outer diameter. The first rotating member 127 may further include a recessed hex portion 158 in the distal end operable to receive the second rotating member 134 and the spring 132. While the figure depicts a recesses that is hexagonally shaped, the present invention includes any of a number of shapes including lineal, oval, square, rectangular, trapezoidal, X-shaped, etc., or can be polygonal and provide for various angles that cause a lineal increase or decrease in the length of the overall strut. The polygonal shape can include shapes with 3, 4, 5, 6, 7, 8, 9, 10, 11, 12, 13, 14, 15, 16, 17, 18, 19, 20, 21, 22, 23, 24, 25 or more sides to provide very gross, moderate or detailed distraction of the strut. In an embodiment, the second rotating member 134 may be a hex drive bushing. The first rotating member 127 further includes an internal recess extending from the proximal end of the first rotating member 127, wherein a proximal portion of the internal recess is generally round in shape with two flat sides 160 approximately 180° from each other about a circumference of the proximal portion and is operable to mate with the indexing flange 131.

When the adjustment mechanism 126 is in a first, locked position, the flat sides 160 of the proximal end of the internal recess of the first rotating member 127 mate with the flat sides of the indexing flange 131, thereby preventing rotation of the first rotating member 127 relative to the inner adjustment sleeve 122. Although the disclosed indexing flange and the proximal portion of the internal recess are generally round in shape with two flat sides approximately 180° from each other, it is to be understood that the indexing flange and the proximal portion of the internal recess of the first rotating member may be any shape operable to mate with each other. For example, both may be shaped in any polygonal shape, such as a triangle, square, pentagon, hexagon or the like. In addition, both may be shaped as a generally round shape with one flat side about a circumferential portion. These shapes can be used to accomplish the gradual rotation of the rotation mechanism 126 in predetermined angular increments, such as 15°, 20°, 30°, 45°, 60°, 90°, etc. By making these adjustments, the length of the strut can be gradually and accurately adjusted.

The second rotating member 134 may include a hex-shaped head 136 at a distal end operable to be received in and mate with the recessed hex portion 158 of the first rotating member 127. The hex-shaped head 136 may have a diameter greater than a diameter of a proximal portion 137 of the second rotating member 134. According to other embodiments, the hex-shaped head 136 and second rotating member 134 may have other polygonal shapes, so long as they mate with each other and prevent the rotation of the second rotating member 134 with respect to the head 136. The second rotating member 134 may further include a sidewall of an internal recess 135 in the proximal portion 137 comprising mating barbs 130 operable to mate with the mating barbs 125 of the adjustment sleeve 122. The mating barbs 125, 130 may be operable to allow the second rotating member 134 to rotate about the inner adjustment sleeve 122 but not to allow axial translation of the second rotating member 134 relative to the inner adjustment sleeve 122. The second rotating member 134 may further include an threaded aperture 138 defined from a distal end of the second rotating member 134 to a distal end of the internal recess 135, wherein the threaded aperture 138 is operable to receive and mesh with the threaded elongated member 128.

The spring 132 may be a compression spring and may be wound around the proximal portion 137 of the second rotating member 134. Other embodiments may utilize any mechanical means (e.g., a wave spring or other device) to bias a proximal side of the hex-shaped head 136 to the inwardly extending flange 151. When the spring 132 is in its state of equilibrium and wound around the proximal portion 137 of the second rotating member 134, the spring 132 may have a length extending from a proximal side of the hex-shaped head 136 to a proximal end of the second rotating member 134 and may rest on the inwardly extending flange 151 within the first rotating member 127. The first rotating member 127 is spring biased by the spring 132, thereby keeping the adjustment mechanism 126 in its first, locked position until the first rotating member 127 is forcibly translated distally relative the inner adjustment sleeve 122.

The external fixation connection rod 100 may be assembled so that the spring 132 is first received within the first rotating member 127 from the distal end through the recessed hex portion 158 until a proximal end of the elongated compression spring 132 rests on the inwardly extending flange 151 proximate to the proximal end of the first rotating member 127.

Separately, the threaded elongated member 128 may be threaded through the internal recess 135 and the threaded aperture 138 of the second rotating member 134 from a proximal end until a shoulder portion 129 located at a proximal end of the threaded elongated member 128 abuts a distal end of the internal recess 135. A diameter of the shoulder portion 129 of the threaded elongated member 128 is greater than a diameter of the threaded aperture 138 of the second rotating member 134 so that the shoulder portion 129 cannot be threaded completely through the threaded aperture 138. When the shoulder portion 129 of the threaded elongated member abuts the distal end of the internal recess 135, the external fixation connect rod 100 is in its fully extended state. From its fully extended state, the external fixation connection rod 100 may be shortened through counterclockwise rotation of the threaded elongated member 128 when the second articulatable joint (not shown) is distal relative to the first articulatable joint (also not shown).

The second rotating member 134 and the threaded elongated member 128 may then be received within the first rotating member 127 and the spring 132 through the recessed hex portion 158 of the first rotating member 127 until the proximal end of the hex-shaped head 136 of the second rotating member 134 rests on a distal end of the spring 132 in its elongated state. Next, the first rotating member 127, the spring 132, the second rotating member 134, and threaded elongated member 128 may together be received in unison onto the tip 119 of the adjustment sleeve 122 so that a proximal portion of the threaded elongated member 128 is received into the axial bore 123 of the inner adjustment sleeve 122 and the mating barbs 125, 130 are interlocked. The orientations of the mating barbs 125, 130 allow the first rotating member 127, the spring 132, the second rotating member 134, and threaded elongated member 128 to be received onto the inner adjustment sleeve 122 during assembly but not removed from the adjustment sleeve 122. As previously mentioned, the mating barbs 125, 130 also allow the second rotating member 134 to rotate about the inner adjustment sleeve 122.

In operation, the length of the external fixation connection rod 100 may be adjusted in a two step process—first through rapid adjustment before the external fixation connection rod 100 is connected to an external fixation ring (not shown) and second by gradual adjustment after the external fixation connection rod 100 is connected to the external fixator ring. In order to perform rapid adjustment, the sleeve fastener 124 is loosened, allowing the inner adjustment sleeve 122 to slidably translate within the outer telescopic housing 118. After the desired length of the external fixation connection rod 100 is approximately set through rapid adjustment, the sleeve fastener 124 is tightened, thereby preventing the inner adjustment sleeve 122 from further translation within the outer telescopic housing 118. After rapid adjustment, the external fixation connection rod 100 is connected to a first external fixator ring (not shown) at the first articulatable joint 102 and connected to a second external fixator ring (not shown) at the second articulatable joint 110. The length of the external fixation connection rod 100 can then be adjusted through gradual adjustment using the adjustment mechanism 126.

Gradual adjustment is performed within the adjustment mechanism 126 by moving the adjustment mechanism 126 from the first, locked position of FIG. 11 to the second, unlocked position of FIG. 12. The first rotating member 127 is spring biased via the spring 132 to keep the adjustment mechanism 126 in the first, locked position of FIG. 11. However, when the first rotating member 127 is forcibly translated distally along a longitudinal axis towards the second articulatable joint 110 and then rotated either clockwise (to lengthen the external fixation connection rod 100) or counterclockwise (to shorten the external fixation connection rod 100), the adjustment mechanism 126 is moved to the second, unlocked position. When the first rotating member 127 is translated distally, the compression spring 132 is compressed between the inwardly extending flange 151 of the first rotating member 127 and the proximal end of the hex-shaped head 136 of the second rotating member 134. When the spring 132 is compressed, the flat sides 160 of the proximal end of the internal recess of the first rotating member 127 are translated distally relative to the flat sides of the indexing flange 131 and become disengaged from the flat sides of the indexing flange 131. When the first rotating member 127 is rotated slightly relative to the inner adjustment sleeve 122, the flat sides 160 of the proximal end of the internal recess of the first rotating member 127 rest on the curved sides of the indexing flange 131, thereby moving the first rotating member 127 to the second, unlocked position.

When the first rotating member 127 is in the second, unlocked position, the first rotating member 127, the spring 132, and the second rotation member 134 are operable to rotate 180° clockwise or counterclockwise about the tip 119 of the inner adjustment sleeve 122 and the threaded elongated rod 128. The threaded elongated rod 128 is prohibited from rotating because it is affixed to the second external fixator ring and the inner adjustment sleeve 122 is prohibited from rotating because it received within the outer telescopic housing 118 that is affixed to the first external fixator ring. Therefore, clockwise rotation of the first rotating member 127, the spring 132, and the second rotation member 134 about that tip 119 of the inner adjustment sleeve 122 and the threaded elongated rod 128 causes the threaded elongated rod 128 to be translated out of the axial bore 123 of the inner adjustment sleeve 122, thereby lengthening the external fixation connection rod 100. Counterclockwise rotation of the first rotating member 127, the spring 132, and the second rotation member 134 about that tip 119 of the inner adjustment sleeve 122 and the threaded elongated rod 128 causes the threaded elongated rod 128 to be translated into the axial bore 123 of the inner adjustment sleeve 122, thereby shortening the external fixation connection rod 100.

After the first rotating member 127 is rotated, e.g., 180° clockwise or counterclockwise, the flat sides 160 of the proximal end of the internal recess of the first rotating member 127 again align with the flat sides of the indexing flange 131, and the spring bias of the spring 132 proximally translates the first rotating member 127 back to the first, locked position with, e.g., an audible "click." Although the gradual adjustment mechanism 126 depicted in FIGS. 9-12 index and returns to the first, locked position every half turn or 180°, it is to be understood that different shapes of the proximal end of the internal recess of the first rotating member 127 and the indexing flange 131 may be used to enable locking at different intervals, including 15°, 30°, 45°, 60°, 90°, 120°, etc. The shape of the indexing flange can be selected to provide one 180° clockwise or counterclockwise interval using a shape that is, e.g., lineal, oval, square, rectangular, trapezoidal, X-shaped, etc., or can be polygonal and provide for various angles that cause a lineal increase or decrease in the length of the overall strut. The polygonal shape can include shapes with 3, 4, 5, 6, 7, 8, 9, 10, 11, 12, 13, 14, 15, 16, 17, 18, 19, 20, 21, 22, 23, 24, 25 or more sides to provide very gross, moderate or detailed distraction of the strut. In certain embodiments, both ends of the strut can include the adjustment mechanism 126 (not depicted), or the adjustment mechanism 126 can be internal to the strut (also not depicted).

Figure 13:
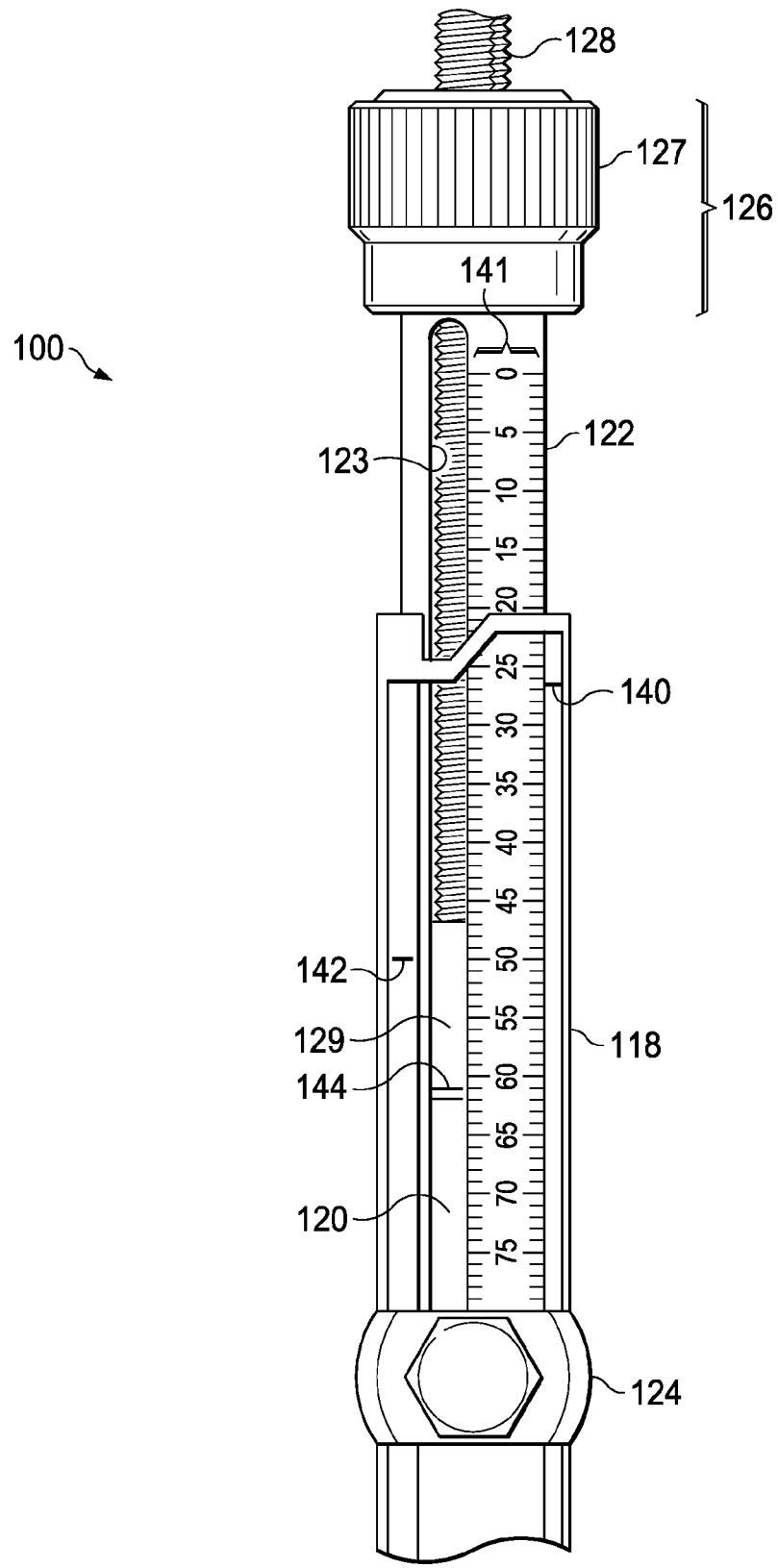
FIG. 13 is a perspective view of a gradual adjustment scale of the external fixation connection rod of FIG. 9.

FIG. 13 is a perspective view of an adjustment scale of the external fixation connection rod 100 of FIGS. 9-12. The adjustment scale includes a series of indicators 141, a rapid adjustment mark 140, an adjustment range midpoint mark 142, and a gradual adjustment mark 144. The series of indicators 141 may comprise a series of numbers and/or tick marks that may be printed on a surface of the inner adjustment sleeve 122 that are visible through the telescopic housing adjustment aperture 120. The series of indicators may be operable to indicate a relative length of the external fixation connection rod 100 during rapid and gradual adjustment. The rapid adjustment mark 140 may be located on the outer telescopic housing 118 and may be proximate to a first side of the series of indicators 141. The rapid adjustment mark 140 indicates the amount of extension of the external fixation connection rod 100 of the acute stage during rapid adjustment. The gradual adjustment mark 144 may be located on the proximal end of the shoulder portion 129 of the threaded elongated member 128 received within the axial bore 123 of the inner adjustment sleeve 122 and may be proximate to a second side of the series of indicators 141. The gradual adjustment mark 144 indicates the amount of gradual extension of the threaded elongated rod 128 that is still available. The adjustment range midpoint mark 142 may be located on the inner adjustment sleeve 122 and indicates a preset position at one half of full extension so that the external fixation connection rod 100 may initially have the same range for extension or retraction.

The indicators 141 indicate the length of the external fixation connection rod 100 as a relative value, rather than the distance from some predetermined specific length. The indicators 141 do not necessarily have to be based on a traditional measuring system, or indicate the effective length of the external fixation connection rod 100 at all. For instance, the indicators 141 could indicate the percentage of total rod extension, or daily increments for cases where the translation takes place over an extended period of time. Reference to a neutral position can be useful to set the base members at a predetermined "neutral" position.

Advantageously, when a plurality of the external fixation connection rods 100 depicted in FIGS. 9-13 are connected between first and second external fixator rings, each adjustment mechanism 126 remains in its first, locked position until forcibly translated and rotated to its second, unlocked position. This configuration prevents the external fixation connection rods 100 from accidentally being lengthened or shortened by accidental contact or when the external fixator rings and the external fixation rods 100 are twisted during normal use after installation.

Furthermore, a doctor may give a patient a prescription for adjusting each external fixation connection rod 100 that the patient can then adjust himself. For example, on a certain day, the prescription may call for a first external fixation connection rod 100 to be lengthened two clicks, second and third external fixation connection rods 100 to be lengthened one click, a fourth external fixation connection rod 100 to be left alone, and fifth and sixth external fixation connection rods 100 to be shortened one click. The patient can then quickly and easily adjust each external fixation connection rod 100 with precision based on his prescription from home without having to visit the doctor for each adjustment.

The present disclosure also includes embodiments for maintaining the orientation of first and second fixator rings for immobilizing bone segments. One exemplary embodiment includes providing a connecting rod comprising a telescopic housing having an axial bore defined therethrough; an adjustment sleeve slidably disposed within the axial bore, the adjustment sleeve and the telescopic housing; and an externally threaded elongated member threadably coupled the adjustment sleeve. A first joint is coupled to an end portion of the housing, and a first rotating member is received in the first joint. Furthermore, the first rotating member comprises a first connection mechanism operable to releasably couple the first rotating member to the first fixator ring and substantially limit the rotational movement of the first rotating member. A second joint is coupled to an end portion of the housing, and a second rotating member is received in the second joint. Furthermore, the second rotating member comprises a second connection mechanism operable to releasably couple the second rotating member to the second fixator ring and substantially limit the rotational movement of the second rotating member. The disclosed embodiment further includes adjusting the longitudinal position of adjustment sleeve relative to the telescopic housing, and releasably coupling the adjustment sleeve to the telescopic housing using a sleeve fastener. The disclosed embodiment further includes using the first connection mechanism to releasably couple the first rotating member to the first fixator ring and substantially limit the rotational movement of the first rotating member, and using the second connection mechanism to releasably couple the second rotating member to the second fixator ring and substantially limit the rotational movement of the second rotating member.

The methods of the present disclosure may be performed with a subject, e.g., a human or another vertebrate animal. One or more bones (of the subject) to be fixed may be selected. Any suitable bone(s) may be selected, such as a long bone(s) and/or at least a pair of bones connected via an anatomical joint. Exemplary bones include leg bones (femur, tibia, and fibula), arm bones (humerus, radius, and ulna), foot bones (calcaneus, talus, metatarsals, and phalanges), wrist/hand bones (carpals, metacarpals, and phalanges), etc. In exemplary embodiments, one or more bones including at least one long bone may be selected.

An external fixation device may be constructed along and at least partially around the selected bone(s). The external fixation device may include a plurality of rings fixed in position relative to one another by numerous connecting rods secured to the rings.

The external fixation device may be connected to the selected bone(s). Connection may be performed at any suitable time, such as before, during, and/or after construction of the external fixation device. For example, the external fixation device may be assembled and then connected to bone, or individual external fixation device members or external fixation device sub-assemblies may be connected to the bone before the external fixation device is fully assembled. Connection of the external fixation device to bone may include placing connectors, such as wires, pins, screw, and/or rods, among others, through the skin and into, through, and/or around the selected bone.

The external fixation device may be reconfigured while it is connected to the one or more selected bones. Reconfiguration may include adjusting the length, angle, position, and/or connection site of one or more external fixation device components, particularly connecting rod. In some embodiments, reconfiguration may involve lengthening and/or shortening one or more (or all) connecting rods of the external fixation device. In some embodiments, reconfiguration may involve replacing one or more connecting rods with a different connecting rod(s). The different connecting rod may be of different size, pivotability, adjustability, shape, and/or the like.

The external fixation device may be braced to facilitate reconfiguration. Bracing the external fixation device may stiffen and/or stabilize the external fixation device such that reconfiguration produces fewer undesired changes to the external fixation device structure as the external fixation device is weakened and altered during reconfiguration. Bracing may be performed by a pair of connecting rods of the external fixation device. In some examples, the brace may be configured to be clipped onto the external fixation device members before the brace is fully secured to the external fixation device members. For example, the brace may include one or more external fixation device engagement elements that are biased to opposingly engage one or more respective external fixation device members. In any case, each engagement element may be secured in place on the external fixation device member by operating a user control, manually or with a tool. Furthermore, the relative spacing and angular disposition of the engagement elements may be fixed by operating a user control, either the same user control(s) for securing the engagement element to a frame member or a distinct user control.

In some examples, the brace may include one or more movable joints, and the brace may be installed in engagement with the external fixation device members with one or more of the joints in a movable configuration. The movable joints then may be adjusted to a locked (fixed) configuration. Alternatively, or in addition, the brace may include a plurality of movable joints and one or more of the movable joints may be locked before or during brace placement onto the frame, and one or more other of the movable joints may be locked after brace placement onto the external fixation device.

The brace may be removed after frame reconfiguration. Accordingly, the brace may be installed with the frame (and connecting rod) fixing bone and removed with the frame reconfigured and still fixing bone. The brace thus may be present on the external fixation device for only a fraction of the time that the external fixation device is fixing bone.

It is contemplated that any embodiment discussed in this specification can be implemented with respect to any method, kit, reagent, or composition of the disclosure, and vice versa. Furthermore, compositions of the disclosure can be used to achieve methods of the disclosure.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A connecting rod for an external fixation device, the connecting rod defining a longitudinal axis and comprising:
   a telescopic housing comprising a housing body having an axial bore defined therethrough;
   an inner sleeve slidably disposed within the axial bore of the telescopic housing, the inner sleeve and the telescopic housing being releasably coupled by a fastener, wherein a surface of the inner sleeve further comprises a series of indicators operable to indicate a relative value associated with a state of the connecting rod during rapid and gradual adjustment;
   an adjustment mechanism rotatably coupled with the inner sleeve;
      wherein the adjustment mechanism is operable to be placed in one or more locked positions at fixed intervals or an unlocked position;
      wherein the adjustment mechanism has a threaded bore defined therethrough; and
      wherein the adjustment mechanism is operable to be rotated about the inner sleeve by the fixed intervals between the locked positions; and
   an externally threaded elongated member threadably coupled with the adjustment mechanism; and
   wherein when the adjustment mechanism is rotated about the inner sleeve during gradual adjustment, the elongated member is translated relative to the adjustment mechanism along the longitudinal axis, thereby lengthening or shortening an overall length of the connecting rod;
   wherein when the fastener is loosened, the inner sleeve can slidably translate within the axial bore of the telescopic housing during rapid adjustment, thereby lengthening or shortening the overall length of the connecting rod.

2. The connecting rod of claim 1, wherein the inner sleeve comprises:
   a sleeve body having an axial bore defined therethrough;
   an indexing flange coupled to a distal end of the sleeve body; and
   a tip coupled to a distal surface of the indexing flange.

3. The connecting rod of claim 2, wherein the adjustment mechanism is disposed about the tip of the inner sleeve and comprises: a first rotating member having an axial bore defined therethrough, the axial bore comprising: a polygonal recess in a distal end; and an inner recess in a proximal end operable to receive the indexing flange of the inner sleeve; a second rotating member having the threaded bore defined therethrough, the second rotating member comprising: a polygonal head at a distal end operable to mate with the polygonal recess of the first rotating member; and a proximal portion comprising an inner recess operable to receive the tip of the inner sleeve.

4. The connecting rod of claim 3, wherein in the one or more locked positions, the inner recess of the proximal end of the first rotating member receives the indexing flange of the inner sleeve, thereby preventing the adjustment mechanism from rotating about the inner sleeve, and wherein in the unlocked position, the first rotating member is distally translated relative to the second rotating member and the inner recess of the proximal end of the first rotating member disengages from the indexing flange of the inner sleeve, thereby allowing the adjustment mechanism to rotate about the inner sleeve.

5. The connecting rod of claim 4, further comprising:
   a biasing member placed adjacent to the proximal portion of the second rotating member;
   wherein when the adjustment mechanism is rotated about the inner sleeve, the adjustment mechanism is biased by the biasing member to return to the one or more locked positions when the inner recess of the proximal end of the first rotating member aligns with and receives the indexing flange of the inner sleeve.

6. The connecting rod of claim 3, wherein the tip of the inner sleeve further comprises a plurality of mating barbs about an outer circumference of the tip.

7. The connecting rod of claim 6, where a sidewall of the inner recess of the second rotating member comprises mating barbs operable to mate with the mating barbs of the tip of the inner sleeve.

8. The connecting rod of claim 7, wherein the mating barbs of the inner sleeve and the mating barbs of the second rotating member prevent axial translation of the second rotating member relative to the inner sleeve.

9. The connecting rod of claim 8, wherein the adjustment mechanism of the connecting rod is operable to be adjusted by a patient.

10. The connecting rod of claim 2, wherein the externally threaded elongated member comprises a threaded portion at a distal end and a shoulder portion at a proximal end, wherein a diameter of the shoulder portion is greater than a diameter of the threaded portion and is operable to be received within an internal recess in a distal end of the tip of the inner sleeve.

11. The connecting rod of claim 1, the telescopic housing comprising a first joint coupled to a proximal end portion of the housing body, and a third rotating member received in the first joint, wherein the third rotating member comprises a first connection mechanism operable to releasably couple the third rotating member to a first fixation ring.

12. The connecting rod of claim 1, the externally threaded elongated member comprising a second joint coupled to a distal end of the externally threaded elongated member, and a fourth rotating member received in the second joint, wherein the fourth rotating member comprises a second connection mechanism operable to releasably couple the fourth rotating member to a second fixation ring.

13. The connecting rod of claim 1, wherein the relative value is a relative length of the connecting rod.

14. A method of adjusting a relative position of first and second external fixation devices, comprising:
   providing a connecting rod having a longitudinal axis and comprising:
      a telescopic housing comprising a housing body having an axial bore defined therethrough;
      an inner sleeve slidably disposed within the axial bore of the telescopic housing, the inner sleeve and the telescopic housing being releasably coupled by a fastener, wherein a surface of the inner sleeve further comprises a series of indicators operable to indicate a relative value associated with a state of the connecting rod during rapid and gradual adjustment;
      an adjustment mechanism rotatably coupled with the inner sleeve;
         wherein the adjustment mechanism is operable to be placed in one or more locked positions at fixed intervals or an unlocked position; and
         wherein the adjustment mechanism has a threaded bore defined therethrough; and
      an externally threaded elongated member threadably coupled with the adjustment mechanism; and loosening the fastener and rotating the adjustment mechanism about the inner sleeve by the fixed intervals between the locked positions, thereby translating the elongated member relative to the adjustment mechanism along the longitudinal axis, thereby lengthening or shortening an overall length of the connecting rod.

15. The method of claim 14, wherein the inner sleeve comprises:
   a sleeve body having an axial bore defined therethrough;
   an indexing flange coupled to a distal end of the sleeve body; and
   a tip coupled to a distal surface of the indexing flange.

16. The method of claim 15, wherein the adjustment mechanism is disposed about the tip of the inner sleeve and further comprises:
   a first rotating member having an axial bore defined therethrough, the axial bore comprising:
      a polygonal recess in a distal end; and
      an inner recess in a proximal end operable to receive the indexing flange of the inner sleeve;
   a second rotating member having the threaded bore defined therethrough, the second rotating member comprising:
      a polygonal head at a distal end operable to mate with the polygonal recess of the first rotating member; and
      a proximal portion comprising an inner recess operable to receive the tip of the inner sleeve.

17. The method of claim 16, further comprising:
receiving the indexing flange of the inner sleeve into the inner recess of the proximal end of the first rotating member, thereby preventing the adjustment mechanism from rotating about the inner sleeve in the one or more locked positions; and
translating the first rotating member distally relative to the second rotating member along the longitudinal axis of the connecting rod and rotating the first rotating member about the inner sleeve, thereby disengaging the inner recess of the proximal end of the first rotating member from the indexing flange of the inner sleeve and allowing the adjustment mechanism to rotate about the inner sleeve in the unlocked position.

18. The method of claim 17, further comprising:
biasing the adjustment mechanism to return to the one or more locked positions with a biasing member that is placed adjacent to the proximal portion of the second rotating member when the adjustment mechanism is rotated about the inner sleeve and when the inner recess of the proximal end of the first rotating member aligns with and receives the indexing flange of the inner sleeve.

* * * * *